(12) United States Patent
Riscalla

(10) Patent No.: US 11,933,674 B2
(45) Date of Patent: *Mar. 19, 2024

(54) SYSTEMS AND METHODS FOR LOGGING TEMPERATURES OF FOOD PRODUCTS

(71) Applicant: Avery Dennison Retail Information Services LLC, Mentor, OH (US)

(72) Inventor: Daniel Riscalla, Orange, CA (US)

(73) Assignee: Avery Dennison Retail Information Services LLC, Mentor, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/175,657

(22) Filed: Feb. 28, 2023

(65) Prior Publication Data

US 2023/0204426 A1 Jun. 29, 2023

Related U.S. Application Data

(60) Continuation of application No. 17/652,852, filed on Feb. 28, 2022, now abandoned, which is a division of
(Continued)

(51) Int. Cl.
| | |
|---|---|
| *G01J 5/02* | (2022.01) |
| *G01J 5/07* | (2022.01) |
| *G01J 5/08* | (2022.01) |
| *G06F 16/58* | (2019.01) |
| *G06Q 10/109* | (2023.01) |
| *G06Q 30/018* | (2023.01) |
| *G06Q 50/12* | (2012.01) |
| *H04W 4/021* | (2018.01) |
| *H04W 4/70* | (2018.01) |

(Continued)

(52) U.S. Cl.
CPC ............. *G01J 5/025* (2013.01); *G01J 5/0265* (2013.01); *G01J 5/0275* (2013.01); *G01J 5/07* (2022.01); *G01J 5/0859* (2013.01); *G01J 5/0896* (2013.01); *G06F 16/5866* (2019.01); *G06Q 10/109* (2013.01); *G06Q 30/018* (2013.01); *G06Q 50/12* (2013.01); *H04W 4/021* (2013.01); *H04W 4/70* (2018.02); *G01N 33/02* (2013.01); *G06F 18/00* (2023.01); *G06V 20/68* (2022.01); *H04L 67/12* (2013.01); *H04N 23/57* (2023.01)

(58) Field of Classification Search
None
See application file for complete search history.

(56) References Cited

U.S. PATENT DOCUMENTS

| | | |
|---|---|---|
| 3,656,344 A | 4/1972 | Johns |
| 6,501,384 B2 | 12/2002 | Chapman et al. |

(Continued)

*Primary Examiner* — Michael Lebentritt

(57) ABSTRACT

Systems and methods are provided for logging temperatures of food products using a temperature assembly including a housing and one or more temperature sensors, e.g., an infrared sensor for surface temperatures and an elongate probe for acquiring a temperature within a food product, and a mobile electronic device including a camera, a communication interface for communicating with the temperature assembly, a processor configured to acquire a temperature reading from the temperature assembly and an image from the camera when the temperature reading is acquired, and memory for storing the temperature reading and image.

9 Claims, 24 Drawing Sheets

Related U.S. Application Data application No. 16/389,873, filed on Apr. 19, 2019, now Pat. No. 11,293,805, which is a continuation-in-part of application No. 15/979,353, filed on May 14, 2018, now Pat. No. 10,444,075, which is a continuation of application No. 15/044,056, filed on Feb. 15, 2016, now Pat. No. 10,060,798.

(60) Provisional application No. 62/660,232, filed on Apr. 19, 2018, provisional application No. 62/116,280, filed on Feb. 13, 2015.

(51) Int. Cl.
*G01N 33/02* (2006.01)
*G06F 18/00* (2023.01)
*G06V 20/68* (2022.01)
*H04L 67/12* (2022.01)
*H04N 23/57* (2023.01)

(56) References Cited

U.S. PATENT DOCUMENTS

| | | |
|---|---|---|
| 7,075,442 B2 | 7/2006 | Lion et al. |
| 7,201,099 B2 | 4/2007 | Harris, Jr. et al. |
| 7,455,225 B1 | 11/2008 | Hadfield et al. |
| 9,625,327 B1 | 4/2017 | Bernstein |
| 9,784,624 B2 | 10/2017 | Niederberger et al. |
| 10,060,798 B1 | 8/2018 | Riscalla |
| 10,067,004 B1 | 9/2018 | Allen |
| 10,444,075 B1 | 10/2019 | Riscalla |
| 11,293,805 B1 * | 4/2022 | Riscalla ............ G06Q 30/018 |
| 2001/0040911 A1 | 11/2001 | Rubenstein |
| 2004/0015318 A1 | 1/2004 | Heller et al. |
| 2005/0091113 A1 | 4/2005 | Mitchell et al. |
| 2005/0103980 A1 | 5/2005 | Schultz et al. |
| 2005/0146065 A1 | 7/2005 | Cochran et al. |
| 2008/0042075 A1 | 2/2008 | Smith |
| 2008/0175301 A1 | 7/2008 | Chen |
| 2009/0190626 A1 | 7/2009 | Bradley et al. |
| 2009/0285260 A1 | 11/2009 | Stone et al. |
| 2010/0289669 A1 | 11/2010 | Saltzman et al. |
| 2015/0120586 A1 | 4/2015 | Schechter |
| 2015/0120597 A1 | 4/2015 | Dertadian |
| 2015/0124852 A1 | 5/2015 | Roshandel et al. |
| 2015/0192475 A1 | 7/2015 | Eisenstadt et al. |
| 2017/0030605 A1 | 2/2017 | Heller et al. |
| 2017/0056970 A1 | 3/2017 | Chin et al. |
| 2017/0060206 A1 | 3/2017 | Lee et al. |
| 2017/0122817 A1 | 5/2017 | Willert et al. |
| 2022/0357293 A1 * | 11/2022 | Bauer ............ G01N 25/00 |

* cited by examiner

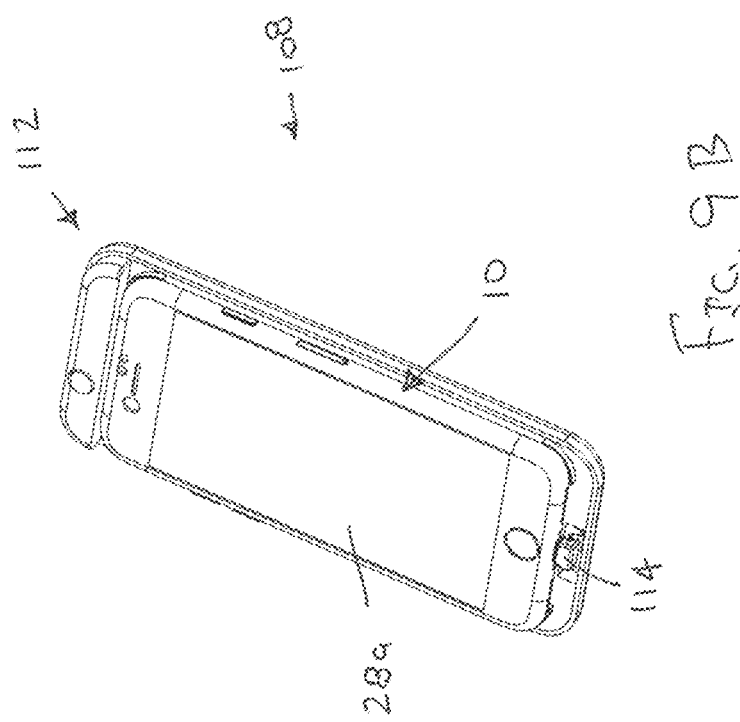

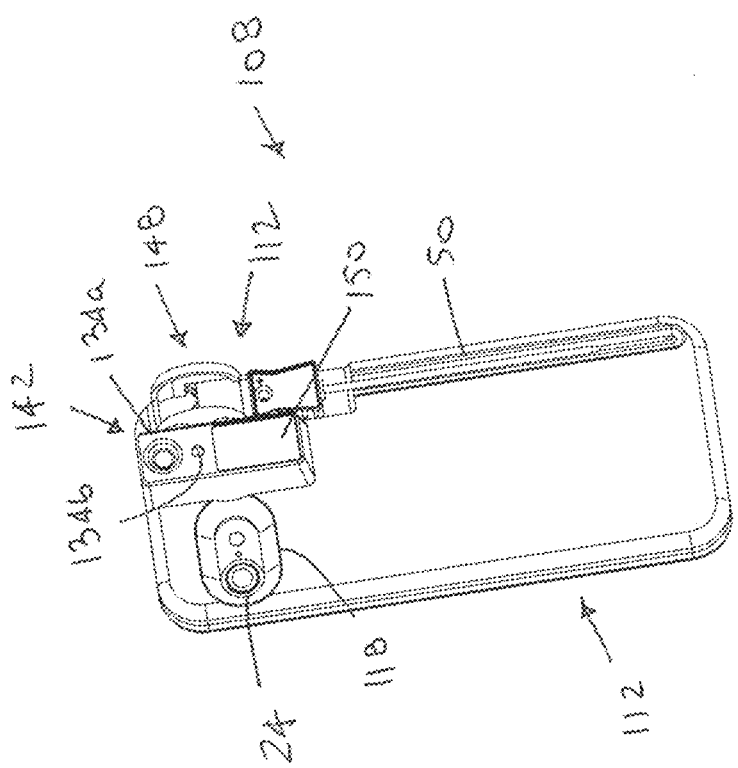

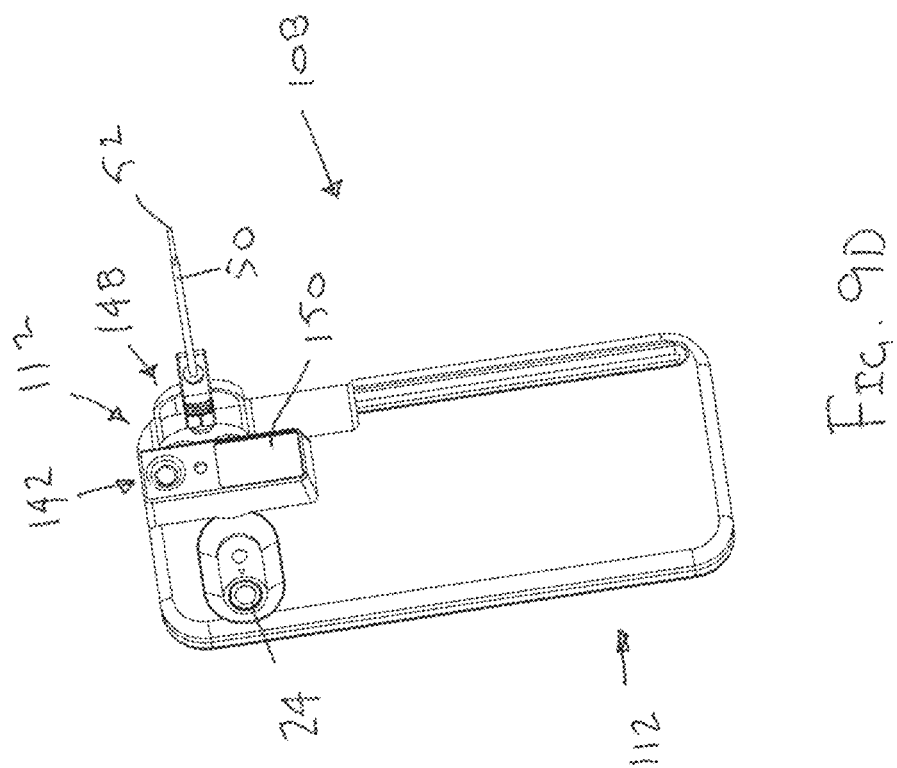

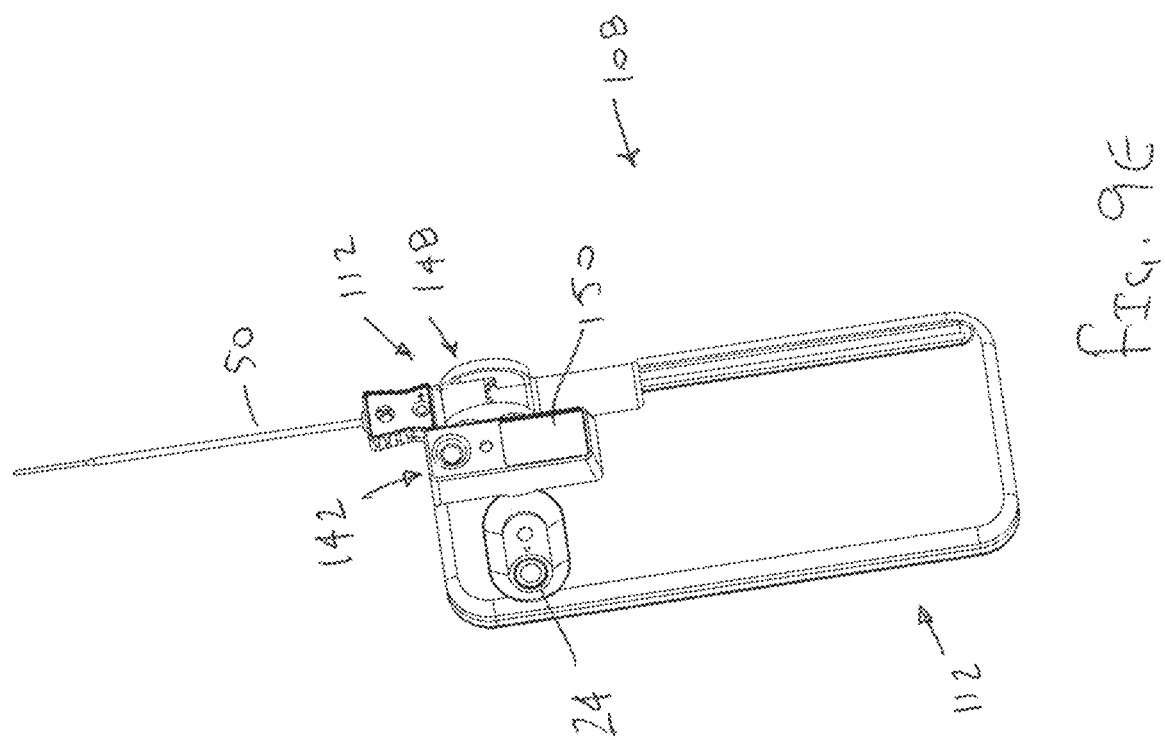

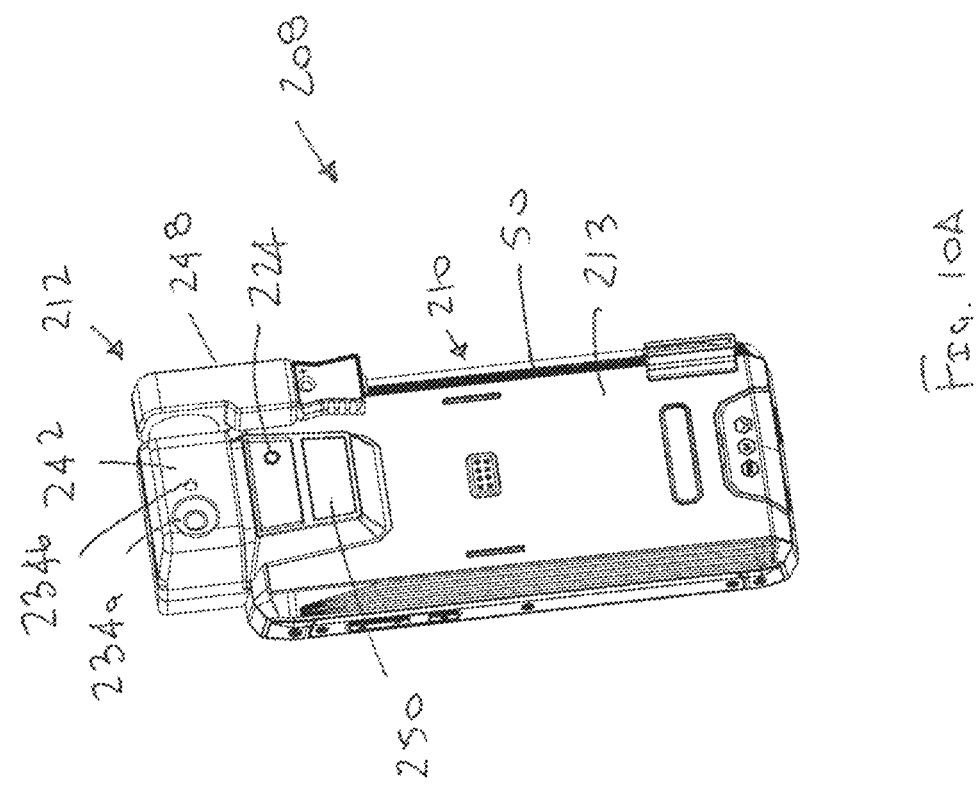

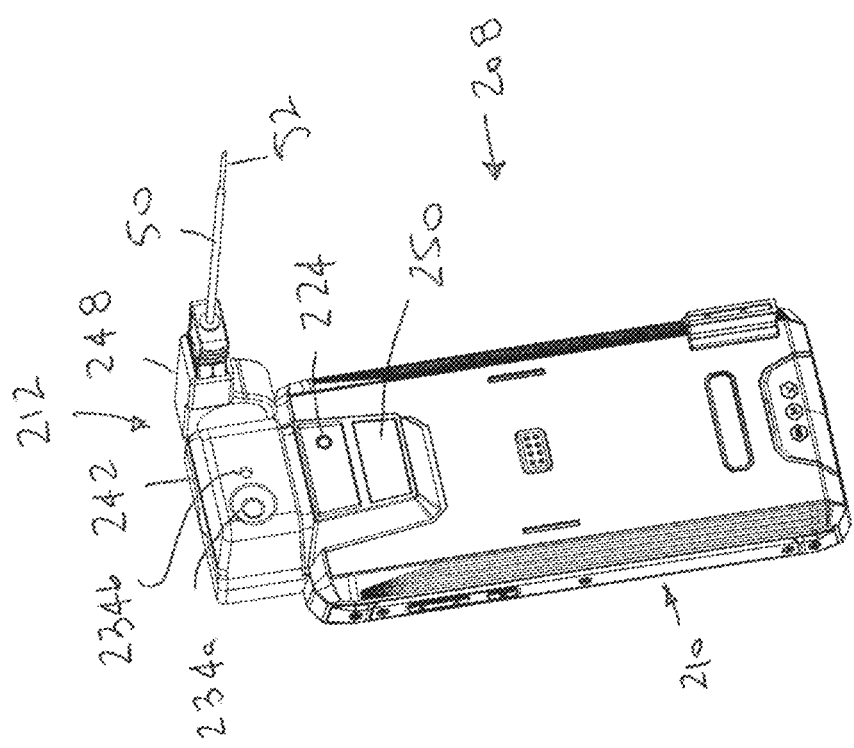

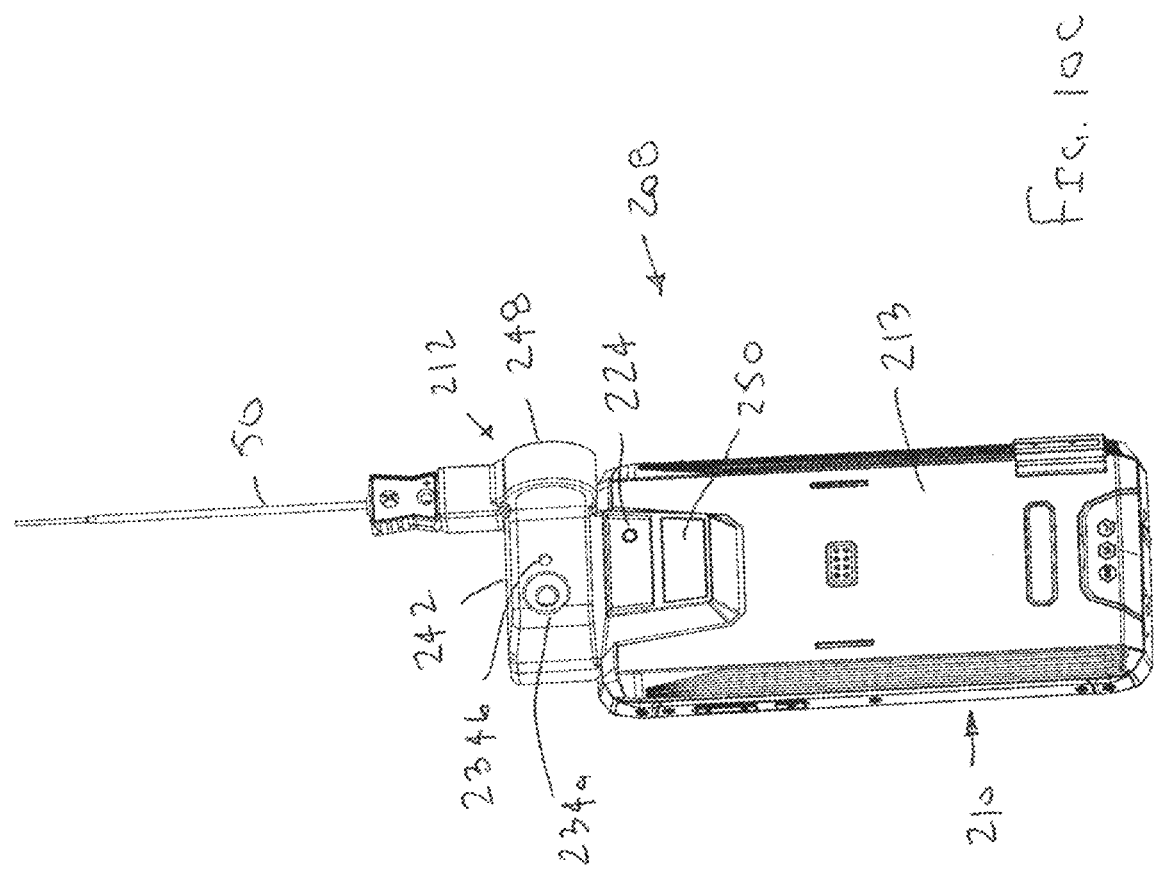

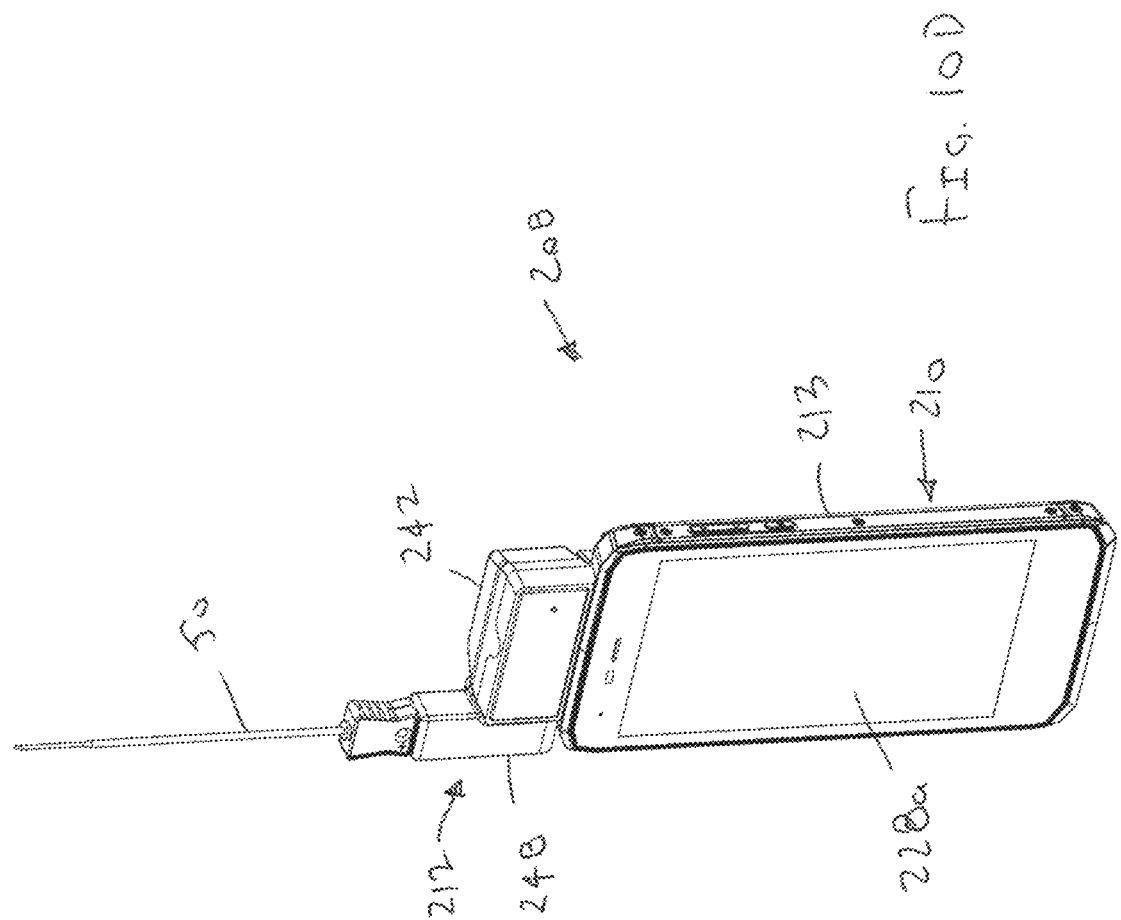

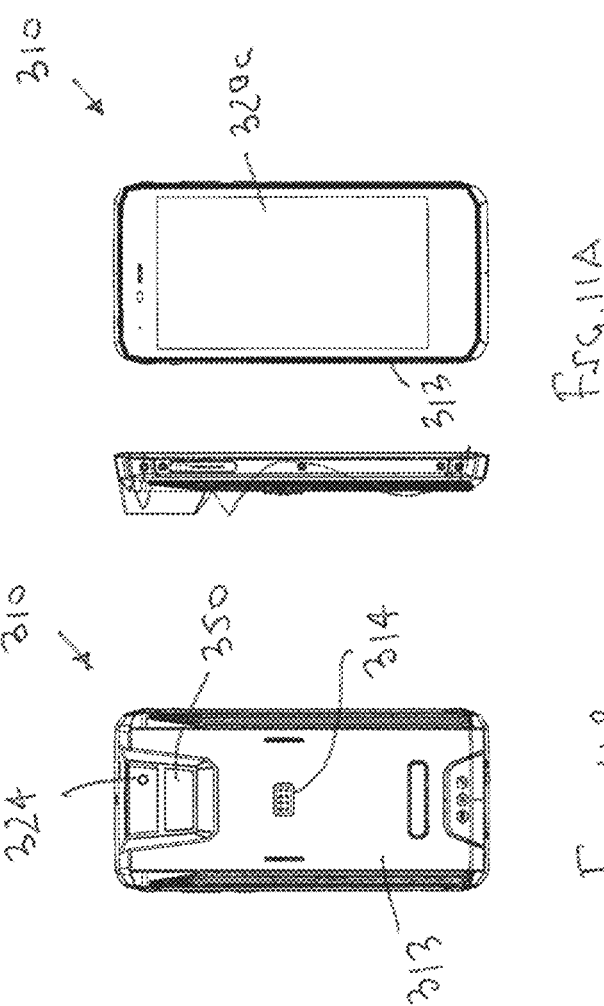

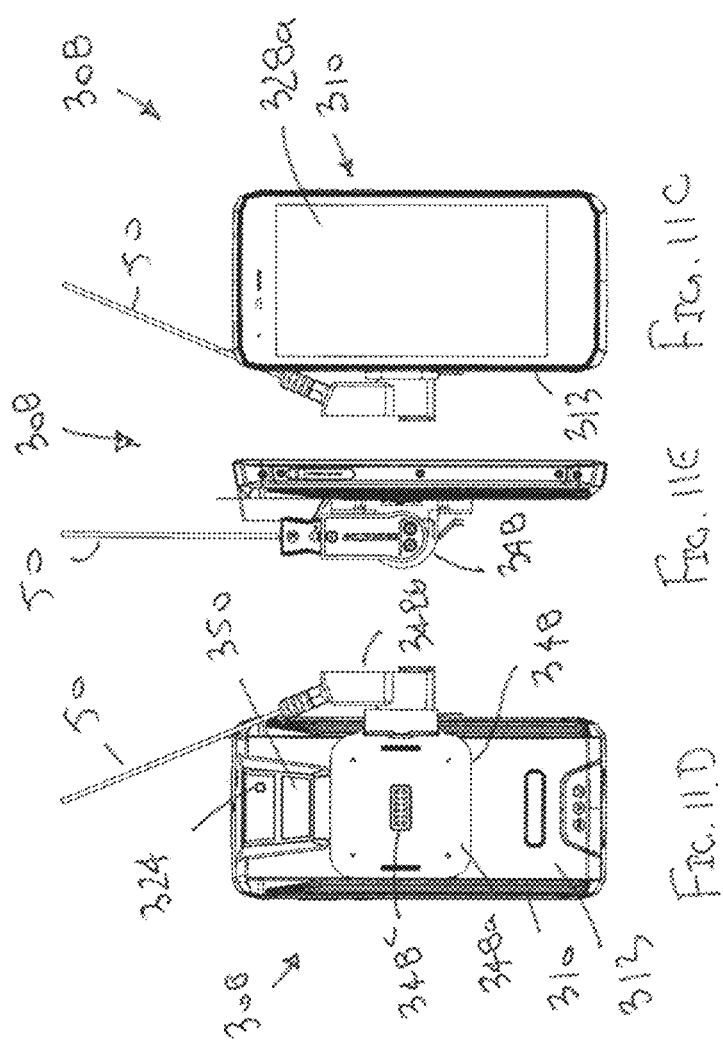

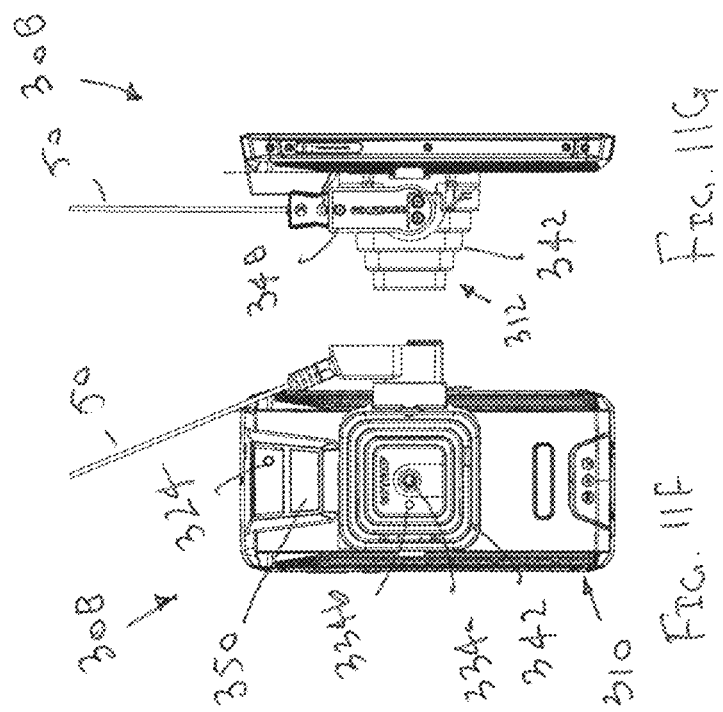

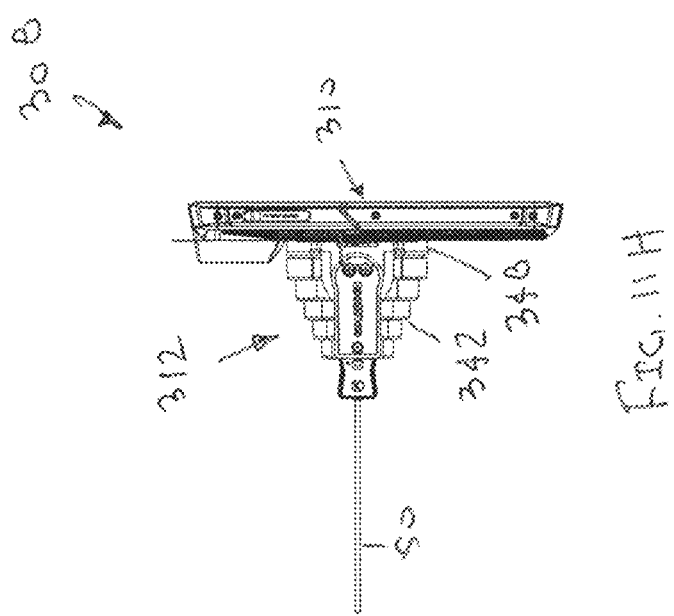

SYSTEMS AND METHODS FOR LOGGING TEMPERATURES OF FOOD PRODUCTS

RELATED APPLICATION DATA

The present application is a continuation of U.S. application Ser. No. 17/652,852 filed Feb. 28, 2022, which is a division of U.S. application Ser. No. 16/389,873 filed Apr. 19, 2019, now U.S. Pat. No. 11,293,805, which claims the benefit of U.S. Provisional Application No. 62/660,232 filed Apr. 19, 2018, and is a Continuation-In-Part of U.S. application Ser. No. 15/979,353 filed May 14, 2018, now U.S. Pat. No. 10,444,075, which is a continuation of U.S. application Ser. No. 15/044,056 filed Feb. 15, 2016, now U.S. Pat. No. 10,060,798, which claims the benefit of U.S. Provisional Application No. 62/116,280 filed Feb. 13, 2015, all of which are incorporated herein by reference in their entireties.

FIELD OF THE INVENTION

The present invention relates to systems and methods for measuring temperatures of food products, e.g., within a restaurant or other establishment where food products or ingredients are stored and/or used. More particularly, the present invention relates to a temperature sensing apparatus that may be coupled to, integrated into, and/or communicate with a mobile electronic device and to systems and methods for acquiring, logging, and/or maintaining temperature records for food products using such an apparatus and/or for providing remedial actions when required, e.g., to increase food safety in real time.

BACKGROUND

Restaurants and other food service businesses generally capture temperatures of food products used by the businesses on a regular basis. Generally, a restaurant that prepares food products from ingredients may acquire and maintain temperature information for ingredients stored at the restaurant, e.g., in a food preparation area where finished products are assembled or otherwise made from the ingredients. For example, a restaurant may establish a policy to acquire and log temperature data multiple times a day to ensure that the food products are stored within desired temperature ranges, e.g., for health and/or other safety reasons. In other cases, such measurement may be mandated by law where measurements must be logged and presented to inspectors upon demand or in the case of an audit.

A thermometer may be used to acquire temperatures of individual food products, e.g., stored in a refrigerated or warmed condition for this purpose. For example, an infrared thermometer may be used to remotely acquire the temperature of food products, or a thermometer probe may be inserted into food products to acquire temperatures. The acquired temperatures may be manually logged, e.g., onto a form, and stored for later review and/or inspection by management, health inspectors, and/or other interested parties.

Such manual acquisition may risk error or deception on the part of the individuals acquiring and logging the temperatures. For example, the user may incorrectly read the thermometer, may enter the data incorrectly into the form, or may even enter false information. This falsification may not be malicious but may simply be a matter of having forgotten to take measurements and being concerned of the potential repercussions. An employee may simply copy over data from prior measurements to complete the mandated record keeping function. It should be noted that the staff employed often has frequent turnover, may not be the most dedicated, or may not be the most meticulous about the functions demanded by the job at hand.

Further, different food types necessitate different measurement techniques. The determination of which measurement method to use, namely a surface temperature reading or a measurement deeper within the food item being measured via an inserted probe must also be determined. For example, raw meats being cooked may require that a central temperature be taken to show that these items are thoroughly cooked. Sliced vegetables may only require a surface temperature reading for an entire bin of produce. If left to the individual, or if the switching between measurement devices is arduous, mistakes can be made, and the wrong systems used for measurement leading to incorrect data and potential food safety issues.

It should also be noted that many existing probe-based systems are typically made up of a solid probe with wired leads attached to a measurement unit. Such a combination requires the use of both hands to operate: one to hold the measurement device and another to take the probe head attached to the wires and to insert it into the food to be measured. In an environment where food products are stored in bins and lids must be opened, or when operating in tight quarters, this two-handed operation can be cumbersome.

Accordingly, systems and methods that facilitate and/or ensure more accurately acquiring, logging, and/or maintaining temperature records for food products would be useful.

Further, systems and methods that allow for both probe and surface measurement using the same system, e.g., allowing for the one-handed operation of the device, would be beneficial and systems and methods that automatically determined the measurement technique required for the food being measured through auto-detection by camera image would be useful.

SUMMARY

The present invention is directed to systems and methods for measuring temperatures of food products, e.g., within a restaurant or other establishment where food products or ingredients are stored and/or used. More particularly, the present invention is directed to a temperature sensing apparatus that may be coupled to, integrated into, and/or communicate with a mobile electronic device and to systems and methods for acquiring, logging, and/or maintaining temperature records for food products using such an apparatus. Optionally, the apparatus may also include a barcode scanner.

In accordance with an exemplary embodiment, a system is provided for logging temperatures of food products that includes a temperature assembly including a housing and a temperature sensor, e.g., an infrared temperature sensor and/or a probe, for acquiring a temperature of a food product; and a mobile electronic device including a camera, a communication interface for communicating with the temperature assembly, a processor configured to acquire a temperature reading from the temperature assembly and an image from the camera when the temperature reading is acquired, and memory for storing the temperature reading and image.

In accordance with another exemplary embodiment, a system is provided for logging temperatures of food products at a physical location that includes a mobile electronic device including a camera; a temperature assembly including a housing configured to removably secure the temperature assembly to the mobile electronic device, and one or both of an infrared sensor and a temperature probe for acquiring a temperature of a food product in a predetermined direction aligned with a field of view of the camera; the mobile electronic device and temperature assembly including one or more communication interfaces for communicating with one another. In addition, the mobile electronic device may include a processor configured to acquire a temperature reading from the infrared sensor and/or temperature prober and an image from the camera when a temperature reading is acquired, and memory for storing the temperature reading and image.

In accordance with yet another embodiment, a method is provided for acquiring temperature data of food products that includes providing a mobile electronic device and a temperature assembly including one or both of an infrared sensor and a temperature probe, the housing coupled to the mobile electronic device; selecting a food product from a menu on a display of the mobile electronic device; and activating the mobile electronic device to acquire a temperature of the selected food product using the temperature probe and substantially simultaneously acquire an image using a camera of the mobile electronic device of the food product.

In accordance with another embodiment, a method is provided for acquiring temperature data of food products that includes providing a mobile electronic device and a temperature assembly including a temperature probe coupled to the mobile electronic device; directing the temperature probe towards a container including a food product, whereupon the food product is automatically identified on a display of the mobile electronic device; and activating the mobile electronic device to acquire a temperature of the identified food product using the temperature probe and substantially simultaneously acquire an image using a camera of the mobile electronic device of the food product. For example, a processor of the mobile electronic device or the apparatus may use object recognition to automatically identify the food product based on the image acquired using the camera and prompt the user to confirm that the correct food product has been identified.

In accordance with still another embodiment, a method is provided for acquiring temperature data of a remote object that includes providing a temperature assembly carried by a mobile electronic device such that an infrared sensor of the temperature assembly is aligned with a field of view of a camera of the mobile electronic device; orienting the infrared sensor towards a target object; and acquiring one or more temperature samples, which optionally may be averaged, to obtain a temperature of the object with the infrared sensor and an image of the object with the camera.

In accordance with another embodiment, a method is provided for acquiring temperature data of food products that includes providing a temperature assembly carried by a mobile electronic device such that an infrared sensor of the temperature assembly is aligned with a field of view of a camera of the mobile electronic device; orienting the infrared sensor towards a container including a food product; and acquiring a temperature of the food product with the infrared sensor and an image of the food product with the camera. Optionally, the food product may be automatically identified and an identifier presented on the display, e.g., along with an image of the food product acquired from the camera and/or along with a dot or other pointer indicating the direction in which the infrared sensor is oriented, e.g., such that the user may confirm that the infrared sensor is oriented towards a desired container and/or food product.

In accordance with yet another embodiment, a method is provided for acquiring temperature data of food products that includes providing a temperature assembly carried by a mobile electronic device such that a tip of a temperature probe extending from the temperature assembly is within a field of view of a camera of the mobile electronic device; inserting the tip of the temperature probe into a food product in a container; and acquiring a temperature of the food product with the temperature probe and an image of the food product with the camera.

In accordance with another exemplary embodiment, a system is provided for logging temperatures of food products that includes a temperature assembly including a housing and one or more temperature sensors, e.g., an infrared temperature sensor and a temperature probe coupled to the temperature assembly, for acquiring a temperature of a food product; and a mobile electronic device including a camera. The temperature assembly may include a mechanism for switching between the temperature probe to be inserted into food products and the infrared temperature sensor, e.g., through a mechanical folding or rotating hinge. In one embodiment, when the temperature probe is directed to the measurement position, the temperature assembly may automatically switch off the infrared temperature sensor. Optionally, the system may be configured to allow the infrared temperature sensor and folding temperature probe to be operated with one hand, e.g., due to the rigid nature of the extended probe and the attachment to the temperature assembly. Optionally, the apparatus may also include a barcode scanner, e.g., a laser barcode scanner integrated into the mobile device or carried by the temperature assembly.

In accordance with another exemplary embodiment, a system is provided for logging temperatures of food products that includes a temperature assembly including a housing and one or more temperature sensors, e.g., an infrared temperature sensor and a temperature probe coupled to the temperature assembly, for acquiring a temperature of a food product; and a mobile electronic device including a camera. During use, the system may use object recognition and/or other algorithms, e.g., via a processor of the temperature assembly and/or mobile device, to recognize food products towards which the camera and temperature sensor are oriented. Upon identification of the food product recognized by the system, the system may direct the user, e.g., by presenting instructions on a display of the mobile electronic device, to use either the infrared sensor to acquire a surface measurement of the food product, or the insert the temperature probe into the food product to acquire temperature readings.

In accordance with another exemplary embodiment, a system is provided for logging temperatures of food products that includes a temperature assembly including a housing and one or more temperature sensors, e.g., an infrared temperature sensor and a temperature probe coupled to the temperature assembly, for acquiring a temperature of a food product; and a mobile electronic device including a camera. Upon confirmation of the food type recognized via the camera, the system may direct the user to insert the probe into an appropriate area of the food product or orient the infrared sensor towards an appropriate area of the food product, e.g., through a target view shown on a display of the mobile device aided by the camera. This target to be measured may be provided for both types of measurements, namely surface or probe-based measurements, and doing so may assure that temperatures are taken in the appropriate location based on the particular food products.

In accordance with another exemplary embodiment, a system is provided for logging temperatures of food products that includes a temperature assembly including a housing and one or more temperature sensors, e.g., an infrared temperature sensor and a temperature probe coupled to the temperature assembly, for acquiring a temperature of a food product; and a mobile electronic device including a camera, which provides remedial actions when temperature measurements are not within acceptable ranges. Remedial actions may include putting the food item back into a refrigerator, discarding the food item, or any number of other instructions and steps. The process for remedial actions may include step by step procedures (e.g., through text, pictures, audio, or video information presented on a display of the mobile device and/or central POS processor at the location) as well as reminders and subsequent alerts and instructions in a pre-established sequence of events.

Optionally, the system may also provide messages to managers and owners of the establishments, e.g., via wireless communications from the mobile device, for informative purposes or for escalation purposes. These messages may include a record of the operators involved with the remedial actions being undertaken as well as logs and pictures.

Other aspects and features including the need for and use of the present invention will become apparent from consideration of the following description taken in conjunction with the accompanying drawings.

BRIEF DESCRIPTION OF THE DRAWINGS

It will be appreciated that the exemplary apparatus shown in the drawings are not necessarily drawn to scale, with emphasis instead being placed on illustrating the various aspects and features of the illustrated embodiments. The drawings illustrate exemplary embodiments, in which:

FIGS. 8A-8E show exemplary images of food products and temperature readings that may be acquired using the apparatus and methods herein.

FIGS. 9A-9C are perspective views of an exemplary embodiment of a system including a temperature sensing apparatus carried by a case to which a mobile electronic device is secured and including a mechanical folding temperature probe in an inactive position.

FIGS. 9D and 9E are perspective views of the system of FIGS. 9A-9C with the temperature probe in first and second active positions, respectively.

FIG. 10A is perspective view of another exemplary embodiment of a system including a laser scanner and a temperature sensing apparatus integrated into a mobile electronic device with a temperature probe in an inactive position.

FIG. 10B is a perspective view of the system of FIG. 10A with the temperature probe directed to a first active position oriented transversely relative to a display of the device.

FIGS. 10C and 10D are perspective views of the system of FIG. 10A with the temperature probe directed to a second active position oriented substantially parallel to the display of the device.

FIGS. 11A and 11E are front and back views, respectively, of an exemplary embodiment of a mobile electronic device including a camera and a laser scanner mounted opposite a display of the device.

FIGS. 11C-11E are front, back, and side views, respectively, of the device of FIGS. 11A and 11B, including a temperature probe assembly mounted to the device.

FIGS. 11F and 11G are back and side views, respectively, of the device of FIGS. 11A-11E, including an infrared temperature sensing assembly mounted to the device adjacent the camera and laser scanner.

FIG. 11H is a side view of the device of FIGS. 11F and 11G, showing the temperature probe directed to an active position.

DESCRIPTION OF THE EXEMPLARY EMBODIMENTS

Turning to the drawings, FIGS. 1A-2B show an exemplary embodiment of a system 8 for logging temperature information for food products, e.g., to facilitate a restaurant or other food services business acquiring, logging, and/or maintaining desired temperature records for ingredients or other food products stored and/or used at the business.

Figure 1B:
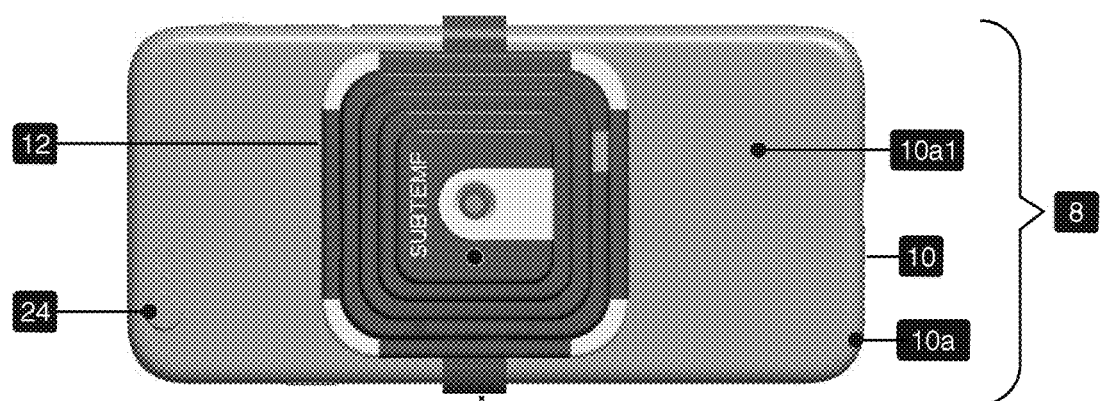
FIGS. 1A and 1B are top and side views, respectively, of an exemplary embodiment of a system including a temperature sensing apparatus coupled to a mobile electronic device.
Figure 1A:
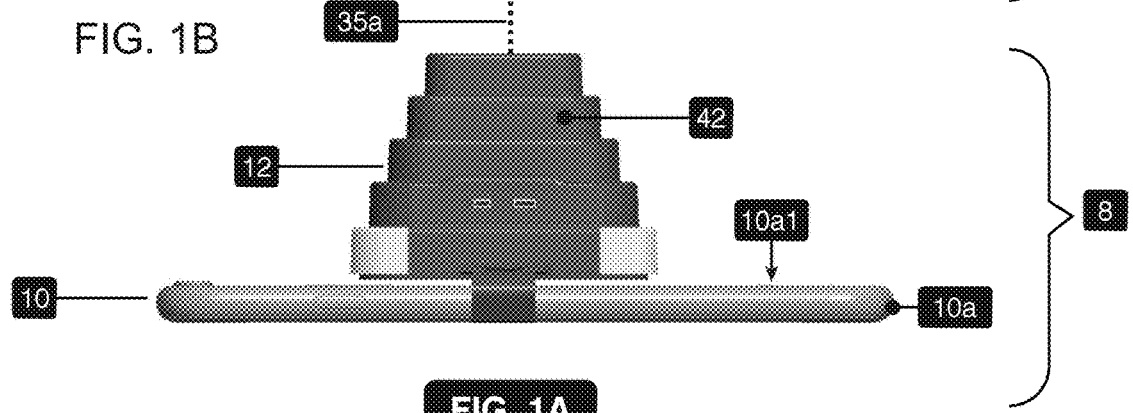
Figure 4:
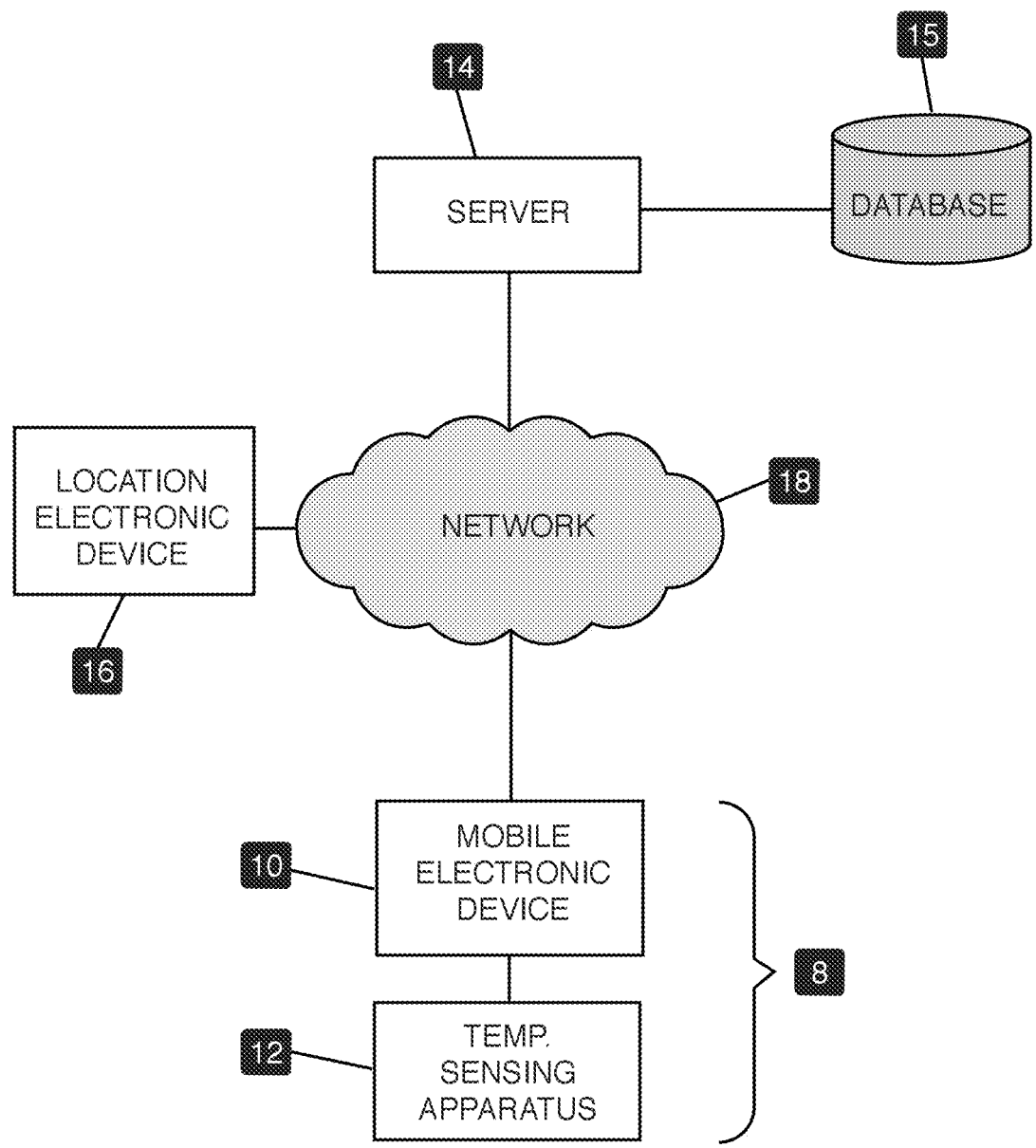
FIG. 4 is a schematic drawing showing an exemplary network architecture within which a system such as that shown in FIGS. 1A and 1B may communicate with other electronic devices to log and/or maintain temperature records.

Generally, as shown in FIGS. 1A and 1B, the system 8 includes a mobile electronic device 10 and a temperature assembly or sensing apparatus 12, which may be coupled to and/or communicate with the electronic device 10 to perform the various functions described herein. Optionally, as shown in FIG. 4, the system 8 may communicate with one or more additional electronic devices, e.g., a remote administrative server 14 and/or a location electronic device 16, e.g., a cash register or other point-of-sale device at the same location as the electronic device 10, via a network 18, as described further elsewhere herein. Optionally, multiple systems 8 may be provided at a single location and/or multiple locations (not shown), which may communicate with the server 14 and/or other devices via the network 18, e.g., to allow multiple systems 8 to acquire temperature information simultaneously and/or to allow multiple locations to store and/or access temperature information in a database 15 maintained by the server 14, e.g., as described elsewhere herein.

The mobile electronic device 10 may be a portable or mobile device, which may be carried by an employee or other user throughout a restaurant or other location to acquire temperature information for desired food products, as described elsewhere herein. In an exemplary embodiment, the mobile electronic device 10 may be a smart mobile device, e.g., an iPhone®, Android®, or other smart phone device, an iPad® or other tablet device, and the like, running a software application performing the various functions and features described herein. Alternatively, as shown in FIGS. 11A and 11B, a custom mobile electronic device 310 may be provided to which one or more modular components may be coupled, as described further elsewhere herein.

Figure 2A:
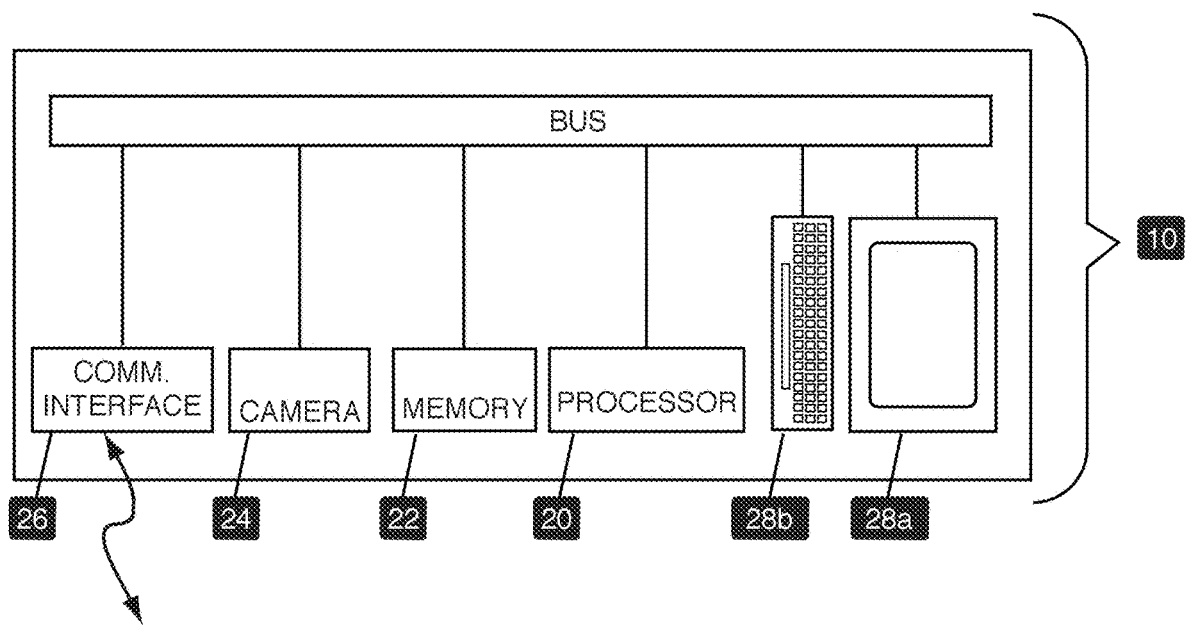
FIGS. 2A and 2B are schematics of exemplary embodiments of a mobile electronic device and a temperature sensing apparatus, respectively.

As shown in FIG. 2A, the mobile electronic device 10 generally includes one or more processors (one processor 20 shown), memory 22, a camera 24, a communication interface 26, and one or more user interfaces 28, e.g., a display or other output device 28*a*, and a touch screen, keyboard, mouse, touch pad, and/or other input device 28*b*. The input device(s) 28*b* may facilitate a user controlling and/or otherwise communicating with the processor 20 or other components of the electronic device 10 and/or the temperature sensing apparatus 12, while the output device(s) 28*a* may allow information to be presented and/or manipulated in a desired manner, e.g., to present a series of menus, fields, pages, and/or other images, as described elsewhere herein. In one embodiment, the electronic device 10 may include a touch screen (not shown) that may act as a display 28*a* and as an input device 28*b*, allowing the user to scroll through menus or images, and/or select icons, e.g., by touching or otherwise selecting corresponding images on the touch screen, as described elsewhere herein.

In an exemplary embodiment, the communication interface 26 includes one or more transceivers, receivers, and/or transmitters, e.g., a short range transceiver for communicating with the temperature sensing apparatus 12 and/or a long range transceiver, e.g., to communicate with the server 14 and/or location electronic device 16 via the network 18 as shown in FIG. 4. In an exemplary embodiment, the short range transceiver may communicate wirelessly using radiofrequency signals, such as Bluetooth or other protocols. Alternatively, a wired communication interface (not shown) may be provided for communicating with the temperature sensing apparatus 12, if desired. For example, in this alternative, the electronic device 10 and/or temperature sensing apparatus 12 may include one or more connectors and/or cables that may be coupled between the electronic device 10 and the temperature sensing apparatus 12, e.g., as described elsewhere herein.

The long range communication interface may allow software and/or data to be transferred between the electronic device 10 and the server 14, the location electronic device 16, and/or other external devices, networks, or information sources. For example, the long range communication interface may communicate via existing networks, e.g., telecommunications networks, the Internet, and the like, as represented by the network 18 shown in FIG. 4. Alternatively, the short range transceiver may be used to communicate with one or more remote devices, the location electronic device 16, and the like via a local wireless network.

Figure 2B:
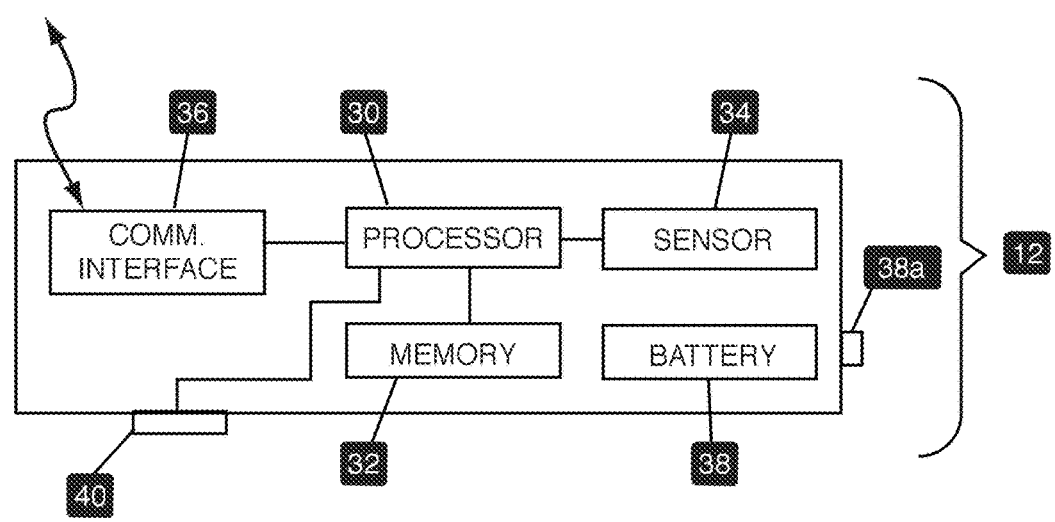

Turning to FIG. 2B, the temperature sensing apparatus 12 generally includes one or more processors (e.g., one processor 30 shown), memory 32, a temperature sensor 34, and a communication interface 36. In an exemplary embodiment, the communication interface 36 may be a short range transceiver that communications with the mobile electronic device 10 via the communication interface 26, e.g., using radiofrequency signals, such as Bluetooth or other protocols.

Figures 3A, 3B:
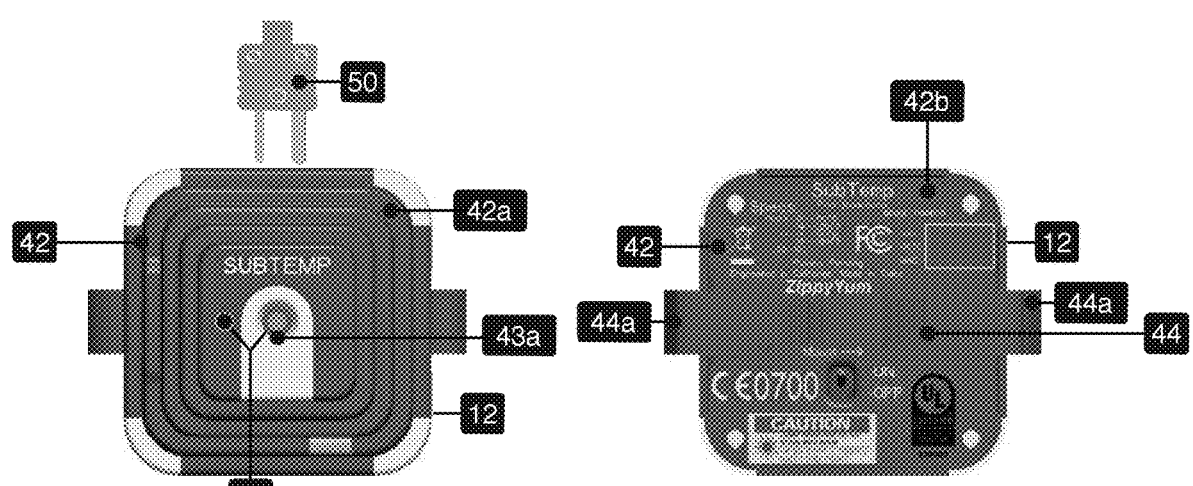
FIG. 3A is a top view of the temperature sensing apparatus of FIGS. 1A and 1B, showing features of the apparatus.
FIG. 3B is a bottom view of the temperature sensing apparatus of FIGS. 1A and 1B, showing a bracket for releasably securing the apparatus to a mobile electronic device.

Optionally, the temperature sensing apparatus 12 may include one or more additional components, e.g., a battery or other power source 38, and/or a probe connector 40, e.g., for coupling a thermocouple or other probe 50 to the apparatus 12, e.g., as shown in FIG. 3A. For example, a k-type thermocouple probe 50 may be coupled to the apparatus 12 that includes a tip (not shown) that may be inserted into a food product to acquire the temperature of the product.

Figure 5A:
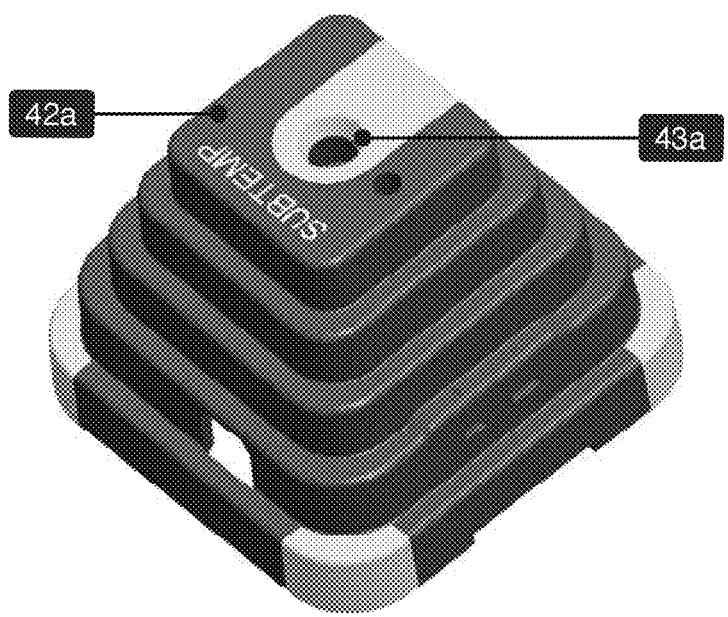
FIGS. 5A-5D show perspective, top, side, and bottom views, respectively, of an exemplary embodiment of a front housing for the apparatus of FIGS. 3A and 3B.
Figure 5B:
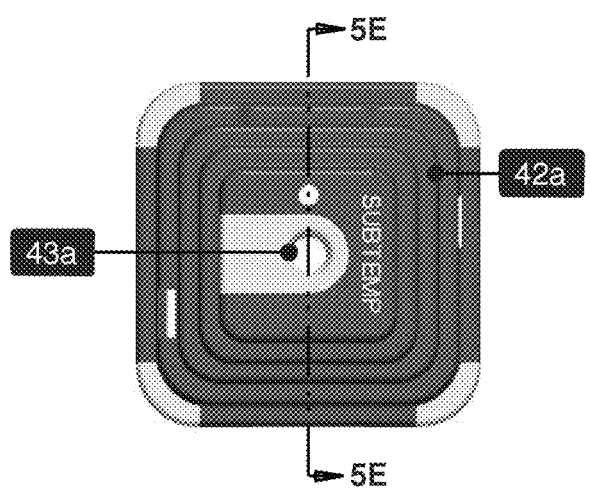
Figure 5D:
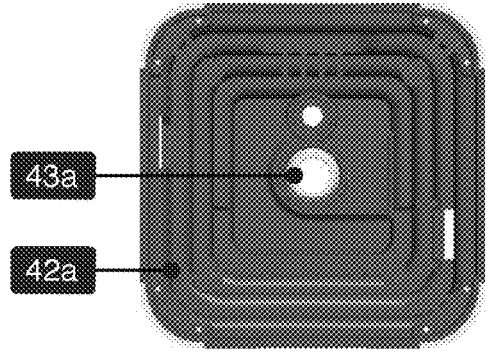
Figure 5C:
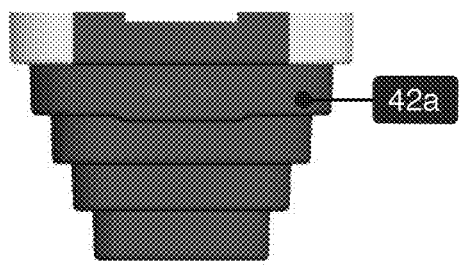
Figure 5E:
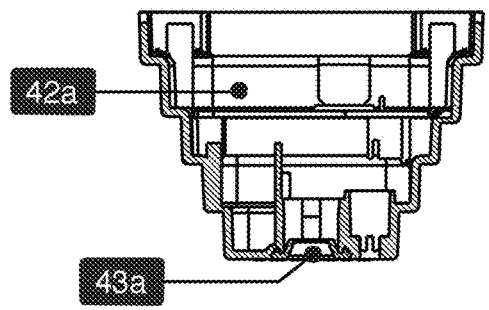
FIG. 5E is a cross-sectional view of the front housing of FIGS. 5A-5D taken along line 5E-5E of FIG. 5B.
Figure 6A:
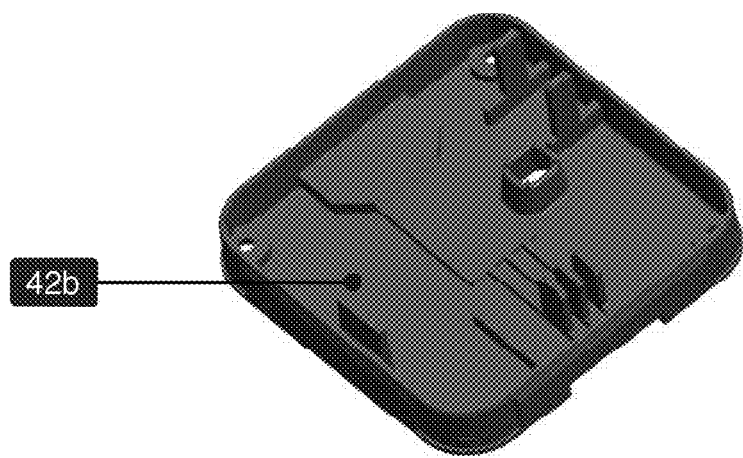
FIGS. 6A-6C show perspective, top, and side views, respectively, of an exemplary embodiment of a back housing for the apparatus of FIGS. 3A and 3B.
Figure 6B:
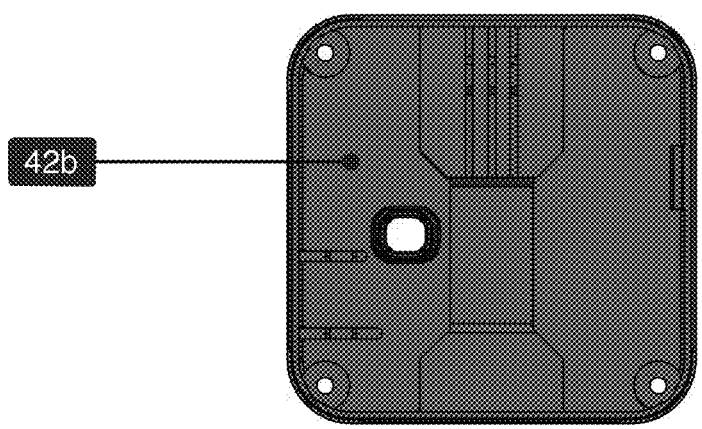
Figure 6C:
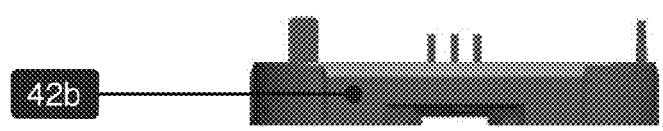
Figure 7A:
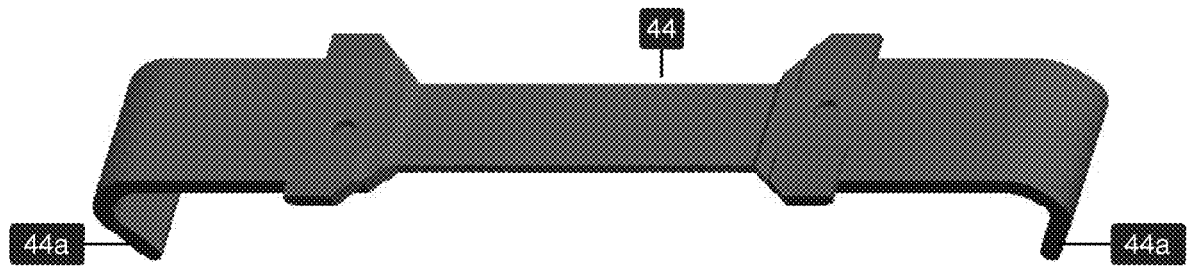
FIGS. 7A-7C show perspective, top, and bottom views, respectively, of an exemplary embodiment of a bracket that may be provided on the apparatus of FIGS. 3A and 3B that include fingers or other elements for coupling the apparatus to a mobile electronic device.
Figure 7B:
Figure 7C:
Figure 7D:
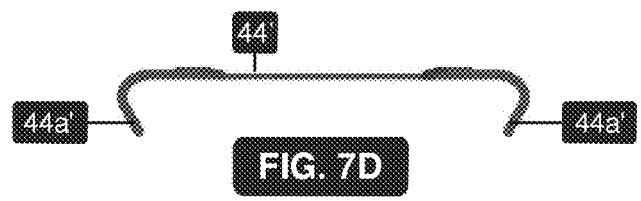
FIGS. 7D-7I show alternative brackets having different/adjustable finger spacing to accommodate mounting the bracket to different size mobile electronic devices.
Figure 7E:
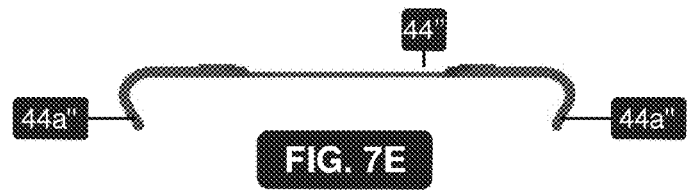
Figure 7F:
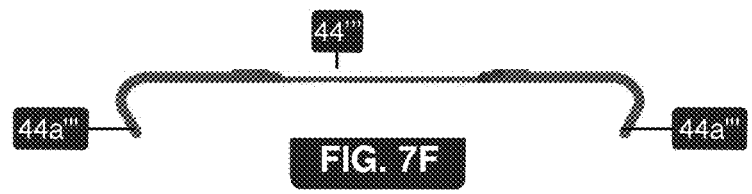

With additional reference to FIGS. 3A and 3B, the components of the apparatus 12 may be contained within a housing 42, e.g., including a top housing 42*a* (e.g., as shown in FIGS. 5A-5E) and a back housing or base 42*b* (e.g., as shown in FIGS. 6A-6C), which may be connected together to substantially seal and/or otherwise protect the components therein. In addition, the housing 42 may include one or more connectors for releasably coupling the apparatus 12 to the mobile electronic device 10. For example, as shown in FIG. 3B, a bracket 44 (e.g., as shown in FIGS. 7A-7C) may be provided on the back housing 42*b* that includes one or more features, e.g., fingers 44*a* that may engage the casing of the mobile electronic device 10. Optionally, as shown in FIGS. 7D-7F, a plurality of brackets 44,' 44," 44'" may be provided that have different shapes and/or configurations that may be selectively coupled to the housing 42 to allow the apparatus 12 to be mounted to different mobile electronic devices. For example, a set of brackets may be provided that include fingers 44*a* having different spacings, e.g., as shown in FIG. 7D-7F as 44*a*', 44*a*" and 44*a*'", and the user may secure the appropriate bracket to the housing 42 that corresponds to the mobile electronic device being used.

Figure 7I:
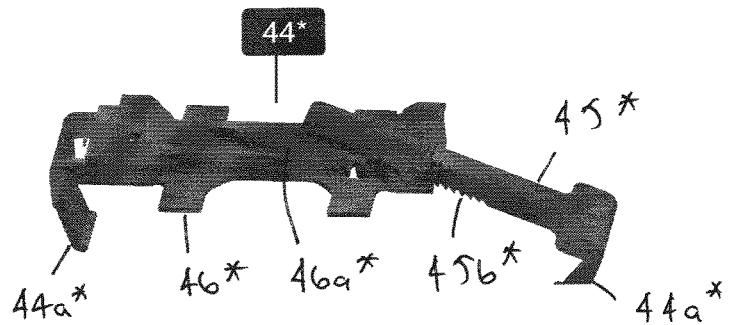
Figure 7H:
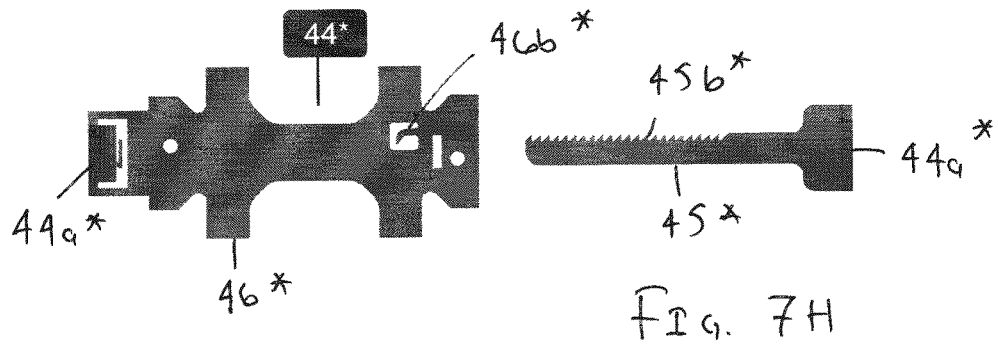
Figure 7G:
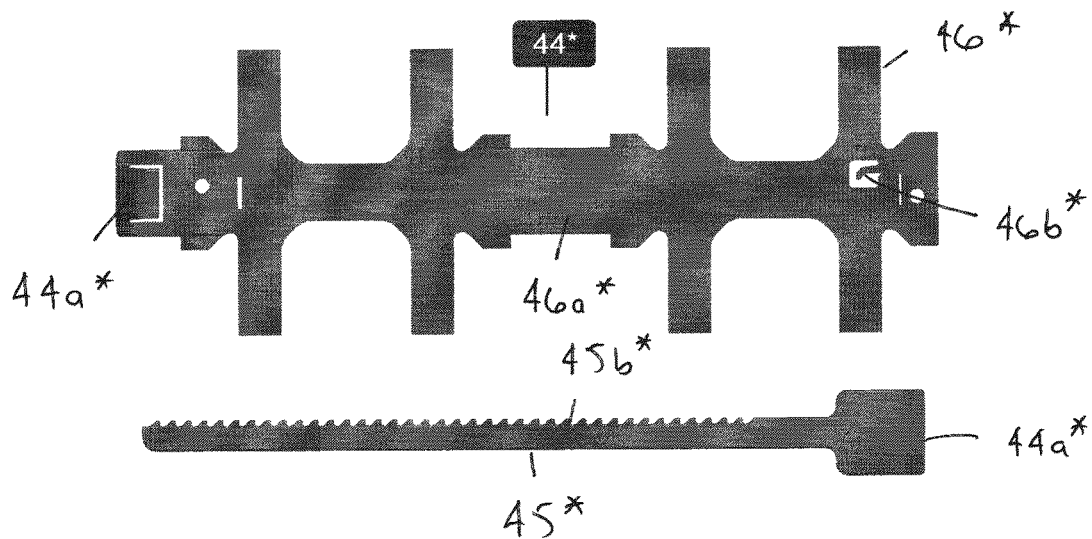

Alternatively, as shown in FIGS. 7G-7I, a single bracket 44* may be provided that is adjustable such that the spacing of the fingers 44*a* may be changed to allow the bracket 44* to be selectively locked to accommodate attachment to different size mobile electronic devices. For example, the bracket may include two sections 45*, 46* that are slidable relative to one another (FIGS. 7G-7I), e.g., to adjust the spacing of the fingers 44***a* to different distances, e.g., as shown in FIGS. 7D-7F. In this alternative, the sections may include cooperating ratchets, detents, and the like (FIGS. 7G-7I) that may fix the fingers 44*a* at predetermined distances. For example, the first section 45* may include a tongue 45*a* including a plurality of detents 45*b* , and the second section 46* may include one or more slots or passages 46*a* that receive the tongue 45*a* and one or more ratchets or detents 46*b* that engage the detents 45*b* to prevent removal of the tongue 45*a*. Optionally, to facilitate removal of the bracket 44*, the first section 45* may be directed out of the plane of the second section 46* to remove the tongue 45*a* from the passage(s) 46*a* and disengage the detents 45*b* , 46*b*. In a further alternative, multiple apparatus 12 may be provided with different brackets substantially permanently secured thereto for mounting each apparatus 12 to a mobile electronic device having a corresponding shape.

Before use, the apparatus 12 may be mounted to a casing 10*a* of the mobile electronic device 10, e.g., by positioning the back housing 42*b* of the apparatus 12 against a corresponding surface of the casing 10*a*, e.g., a back surface 10*a*1 of the electronic device 10 (e.g., opposite the touch screen and/or other user interface of the electronic device 10, not shown, see, e.g., FIG. 1A). For example, a user may position the back 42a of the housing 42 adjacent the back surface 10a1 of the casing 10a adjacent the camera 24 such that the bracket 44 extends across the casing 10a and the apparatus 12 may be pressed against the casing 10a until the fingers 44a of the bracket 44 snap around the casing 10a, thereby securing the apparatus 12 to the electronic device 10, as shown in FIGS. 1A and 1B. The fingers 44a may provide an interference fit with the casing 10a to prevent substantial movement of the apparatus 12 relative to the electronic device 10. Yet, at any time, the user may pull the apparatus 12 away from the electronic device 10, thereby overcoming the interference fit and causing the fingers 44a to resiliently expand and release the apparatus 12 from the electronic device 10. In an alternative embodiment, the bracket 44 may be adjustable, e.g., to change the spacing of the fingers 44a to different distances, e.g., as shown in FIGS. 7D-7I. In another alternative embodiment, a specialized mobile electronic device may be provided that includes the components of the temperature sensing apparatus integrally provided in the electronic device (not shown).

When the apparatus 12 is properly secured to the electronic device 10, the camera 24 may be exposed adjacent the apparatus 12, as shown in FIG. 1A. For example, the camera 24 may have a field of view that includes the line of sight of the sensor 34 of the apparatus 12 (or probe 50 shown in FIG. 3C), e.g., such that a photograph may be taken of a food product when a temperature of that food product is taken, as described further below.

Alternatively, the apparatus 12 may include other structures for removably mounting the apparatus 12 to an electronic device 10. For example, the apparatus 12 may be integrated into a case (not shown), e.g., similar to cases used to hold cell phones or other mobile electronic devices, that may include a recess and one or more detents or other connectors for securing the electronic device to the case with the apparatus 12 secured relative to the camera of the electronic device. Components of the apparatus 12 may be permanently mounted to the case or may be removable from the case, e.g., using one or more mechanical and/or electrical connectors, cooperating magnets, and the like (not shown). For example, FIGS. 9A-9E show an exemplary embodiment of a temperature assembly 112 including a case 113 configured to receive an electronic device 10, as described elsewhere herein.

As best seen in FIGS. 3A and 5E, in an exemplary embodiment, the temperature sensor 34 of the apparatus 12 includes an infrared sensor 34a mounted within the housing 42 such that the sensor 34a is positioned within or oriented towards an opening 43a in the front housing 42, e.g., such that the sensor 34a is configured to acquire temperature data along the line of sight corresponding to sensor axis 35a, as shown in FIG. 1B. In addition, the temperature sensor 34 may include a guide 34b, e.g., a laser pointer 34b, mounted in the housing 42 such that the guide 34b directs a beam of light substantially parallel to or converging on the sensor axis 35a. Consequently, during use, the guide 34b may direct a dot or other image in a direction towards which the infrared sensor 34a is pointed, e.g., to indicate to the user when a food product is within the line of sight of the infrared sensor 34a as well as the camera 24 of the mobile electronic device 10.

Similarly, if a thermocouple or other probe 50 is coupled to the apparatus 12, the probe 50 may have a substantially fixed shape such that a tip of the probe lies within the field of the view of the camera 24. The beam of light from the guide 34b may provide a dot or other image on a food product or surface towards which the tip of the probe is oriented and/or into which the tip is inserted.

Figure 3C:
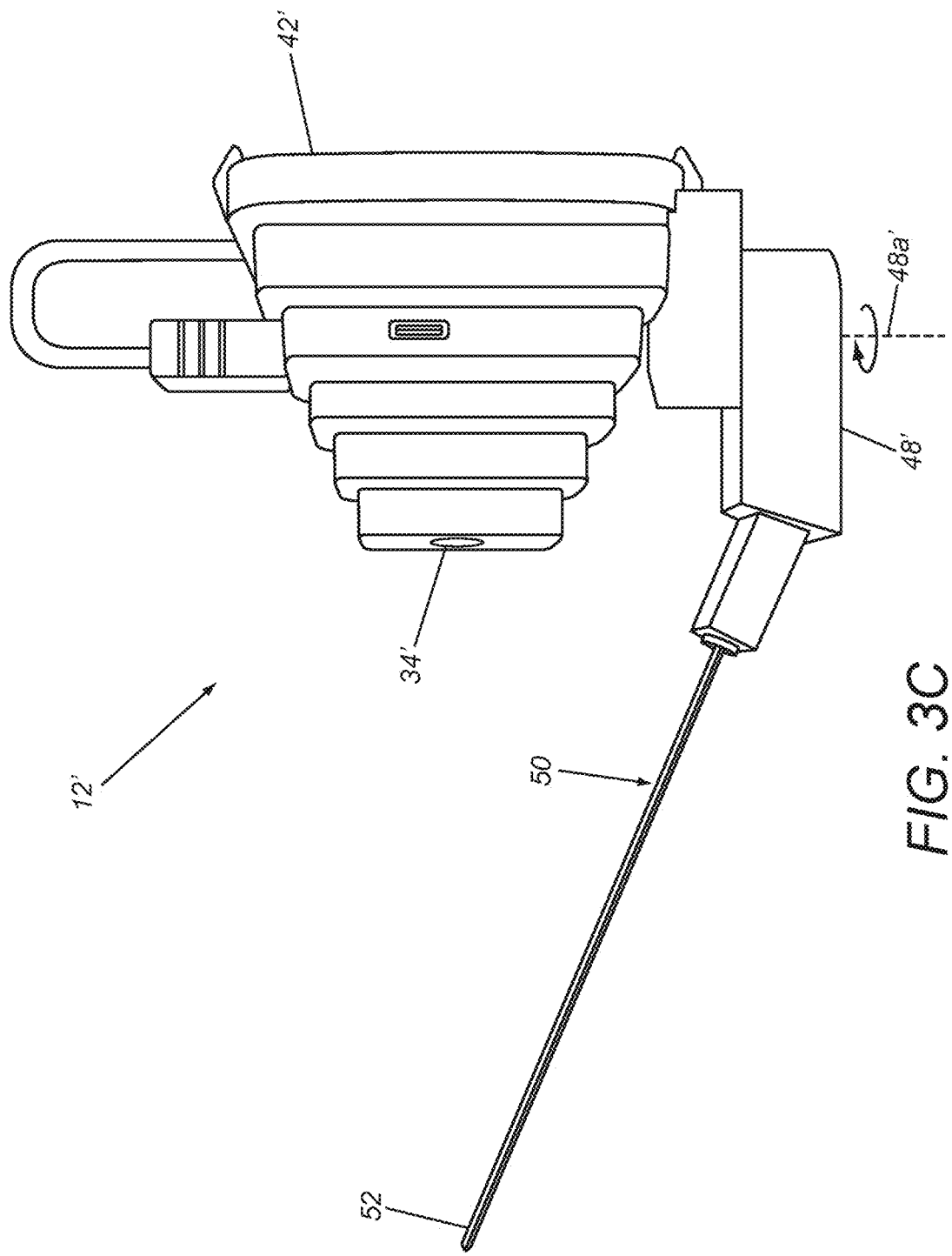
FIG. 3C is a perspective view of an alternative embodiment of a temperature sensing apparatus that includes a mount for a temperature probe that may be directed between one or more positions.

Alternatively, as shown in FIG. 3C, a temperature sensing apparatus 12' may be provided that includes a housing 42' carrying an infrared sensor 34' and including a mount 48' extending from the housing 42' for a temperature probe 50, e.g., a k-type thermocouple sensor. The probe 50 may be removably coupled to the mount 48,' e.g., using one or more pins or other mechanical and/or electrical connectors (not shown), e.g., such that a new probe 50 may be coupled to the mount 48' as desired, e.g., between temperature readings and/or after inserting a tip 52 of the probe 50 into certain food products. Alternatively, the probe 50 may be permanently fixed to the mount 48' if desired.

As shown in FIG. 3C, the mount 48' may be pivotable relative to the housing 42' about an axis 48a,' e.g., such that the probe 50 may be directed between an inactive position and an active position. When the probe 50 is in the active position, shown in FIG. 3C, the tip 52 of the probe 50 lies within the field of view of a camera of a mobile electronic device (not shown) to which the temperature assembly 12' is mounted, while in the inactive position, the probe 50 may be directed out of the field of the view of the camera, e.g., extending along a casing of the electronic device (not shown), e.g., similar to the embodiment shown in FIG. 9C and described further elsewhere herein.

Optionally, in this alternative, the temperature assembly 12' may include a switch or other detector (not shown) that selectively or automatically disables the probe 50 and the infrared sensor 34' for use. For example, when the probe 50 and mount 48' are in the inactive position, the probe 50 may be deactivated, and the infrared sensor 34' may be active and used to acquire temperatures, e.g., using the methods described elsewhere herein. When the probe 50 is directed to the active position shown in FIG. 9C, e.g., by rotating the mount 48' until the probe 50 extending substantially perpendicular relative to a back of the housing 42,' a switch coupled to the mount 48' may automatically enable the probe 50 and disable the infrared sensor 34.' Alternatively, a switch may be provided (e.g., a mechanical switch on the housing 42' or an electronic switch presented on the interface of the electronic device), which may be selected by the user to switch between the two modes.

In the embodiment shown in FIG. 3C, the mount 48' is permanently coupled to the housing 42.' Alternatively, the mount 48' may be removable from the housing 42,' e.g., to facilitate use when the probe 50 is not needed. For example, the housing 42' and mount 48' may include one or more connectors (not shown) that removably fix the mount 48' relative to the housing 42' (and consequently to an electronic device to which the housing 42' is mounted), thereby allowing the mount 48' to be attached and, thereafter, the probe 50 may be directed between the inactive and active positions, as desired. When not needed, the mount 48' may be removed, e.g., when only the infrared sensor 34' is needed.

Returning to FIGS. 1A-2B, at any time before use, a software application may be installed in the mobile electronic device 10, e.g., in memory 22, that allows the device 10 to communicate with the temperature sensing apparatus 12, e.g., to acquire temperature information and/or communicate such information with a remote device, such as the server 14 and/or location electronic device 16. The application may also include a series of menus to facilitate the user acquiring temperature of particular food products and/or locations, e.g., which may be navigated using the user interface 26.

For example, the software application may be initially downloaded into memory 22 via the communication interface 26, e.g., from the server 14 and/or an independent application vendor's server. In addition, the application may be automatically upgraded at desired intervals, e.g., each time the apparatus 12 is coupled to the mobile electronic device 10, when the application is initially launched, when the network 18 is detected, and/or at periodic internals. During any such upgrades, firmware or software in the apparatus 12 itself may be upgraded, if desired, in addition to the application stored in the memory 22 of the mobile electronic device 10.

Once the application is installed and/or updated, the application may be used to acquire temperature data using the apparatus 12. For example, a particular restaurant or business may have a preset list of food products for which temperature data should be acquired, e.g., multiple times per day or at other periodic or regular intervals. In an exemplary embodiment, a Subway® restaurant may include a food preparation area including a plurality of food containers storing particular ingredients for making sandwiches, salads, or other food products. Such ingredients may include meats, cheese, vegetables, and the like, placed in individual containers, which are to be maintained at particular refrigerated temperatures. In addition, some meats or other ingredients, soups, and the like may be placed in individual containers, which are to be maintained at particular heated temperatures. The system 8 may be used to acquire temperature readings for each of these containers, e.g., to create a log of temperatures for the restaurant.

For example, the application may include a menu of such food products, e.g., organized by refrigerated food products and heated food products and/or separated based on different areas within the restaurant. The application may prompt the user when temperature data are scheduled to be acquired, e.g., by providing reminders or other scheduling information on the display 28a of the mobile electronic device 10. In addition or alternatively, a location electronic device 16 (e.g., as shown in FIG. 4), e.g., a point-of-sale device at the restaurant, may provide reminders to users when temperature data is due, e.g., by presenting a pop-up image on a display of the location electronic device 16, which may remain on the display until the scheduled data is acquired and logged. Optionally, the reminder may lock-out the location electronic device 16, e.g., prevent further sales and/or other activities, until the scheduled temperature data is acquired.

Once reminded, the user may obtain the system 8, e.g., by mounting the apparatus 12 to their personal mobile device including the application, by mounting the apparatus 12 to a location-specific mobile device 10, or by simply obtaining the apparatus 12 already mounted to (or integrated into) a mobile device at the restaurant. Alternatively, if the apparatus 12 is modular, i.e., includes separate infrared and probe assemblies, such as the system 308 shown in FIGS. 11A-11H, the user may mount only the components needed for the scheduled readings. In another alternative, as described elsewhere herein, the apparatus 12 may be permanently integrated into a mobile electronic device, such as the system 208 shown in FIGS. 10A-10D, and the user may simply use the integrated device. Optionally, once the apparatus 12 is mounted to the mobile electronic device 10 or otherwise activated, any reminder on the location electronic device 16 may be removed (e.g., instead of locking-out the location electronic device 16).

With continued reference to FIGS. 1A-2B, the user may then activate the apparatus 12, e.g., by turning on the apparatus 12 via a switch or other actuator (not shown), and/or via the menu or interface on the display 28a of the mobile electronic device 10 to obtain the scheduled temperatures. Optionally, when the apparatus 12 is initially turned on, the system may initiate an alignment protocol to ensure that images are acquired within the field of the view of the infrared sensor 34a as indicated by the guide 34b. For example, an image of the field of view of the camera 24 may be presented on the display 28a, which may include a dot from the guide 34b indicating the center of the field of view of the sensor 34a. The user may be prompted to touch the location of the dot on the display 28a, thereby informing the processor 20 of the center of the field of view. The processor 20 may then ensure that images including the dot are acquired during subsequent use.

Once activated, a menu may be presented on the display 28a from which the user may select the food products and acquire temperatures of the selected food products stored within respective containers at the restaurant. Alternatively, the food products may be presented in a preset order such that the user sequentially acquires the temperatures of the food products by navigating through the menu.

When an individual temperature is to be acquired, with the appropriate food product identified on the menu, the sensor 34 and camera 24 may be oriented towards the food product and/or its container. Optionally, the apparatus 12 may be activated from a dormant state, e.g., by selecting a button on the apparatus 12 or on the menu on the display 28a. Optionally, an indicator light may be provided on the apparatus 12, e.g., to confirm when the apparatus 12 is ready to be used. The user may then activate the apparatus 12 to acquire the temperature. In addition and/or optionally, the system 8 may acquire an image of the food product and/or container with the field of view of the camera 24 to confirm that the food product matches the menu selection presented on the display 28a before allowing temperature acquisition, as explained below. Once the food product has been confirmed, the system 8 may allow the user to proceed to acquiring the temperature.

When the apparatus 12 is activated, the temperature sensor 34 may acquire a temperature of the food product within the line of sight of the sensor 34, e.g., using the infrared sensor 34a. Optionally, the apparatus 12 may take multiple temperatures within the field of view and generate an average of the multiple temperatures, which is recorded as the actual temperature. Substantially simultaneously, the camera 24 may acquire an image of the food product towards which the sensor 34 is oriented. The processor 20 of the mobile electronic device 10 may save the temperature and image together in memory 22, thereby providing a record of the food product associated with the acquired temperature. Optionally, the processor 20 may associate a time stamp, food product identifier, user identifier, and/or other information with the temperature/image record, e.g., to provide additional information regarding a particular temperature reading.

Figures 8A, 8B:
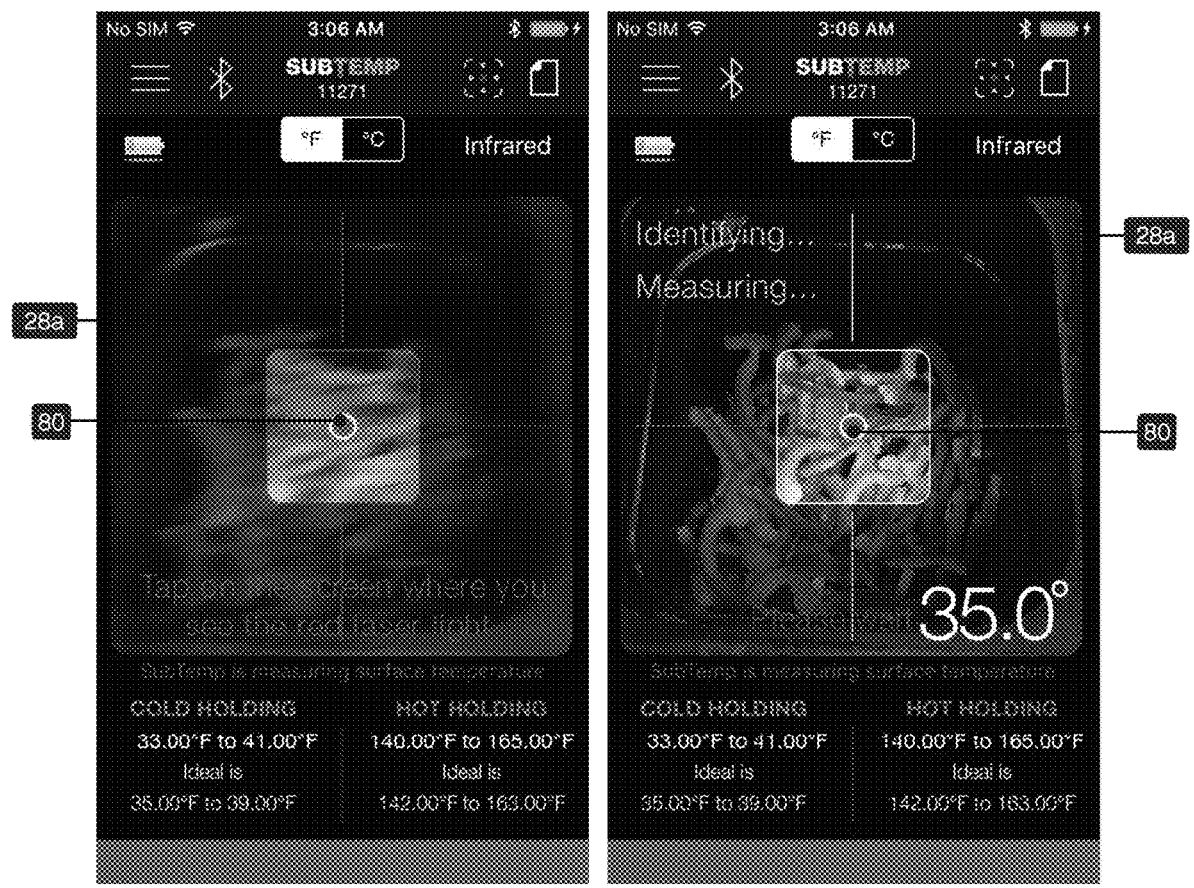

Optionally, the processor 20 may automatically identify a food product within the field of view of the camera 24 before temperature acquisition, e.g., using a database of images, object recognition, and/or other algorithms. For example, as shown in FIGS. 8A and 8B, when the user points the camera 24 towards a container of food products, e.g., green peppers, the processor 20 may identify the food product (green peppers) in the camera images, e.g., indicate that the food product is being identified, as shown in FIG. 8A, and automatically prompt the user that this is the intended food product, as shown in FIG. 8B. Once the user confirms the food product, the processor 20 may automatically acquire the temperature using the sensor 34 or upon activation by the user. Optionally, a real-time temperature reading may be presented on the display, e.g., as shown in FIGS. 8A-8E. Thus, this option may ensure that the temperature data is acquired for the correct food product, which may reduce user error.

In addition or alternatively, real-time images of the food product and/or its container may be presented on the display 28a of the mobile electronic device 10, e.g., to facilitate the user accurately orienting the sensor 34 towards the food product. For example, as shown in FIGS. 8A-8E, the processor 20 may superimpose a graphic 80, e.g., a dot, circle, or other character on the images, e.g., surrounding the dot from the guide 34b, to assist the user. Optionally, the processor 20 may analyze the images, e.g., to ensure that the sensor 34 is oriented properly to reduce the risk of inaccurate temperature readings. For example, if the sensor 34 is oriented towards the wall of a stainless steel container rather than into the food products in the container, temperature readings may be inaccurate due to light being reflected by the stainless steel wall. The processor 20 may prompt the user on the display 28a when this occurs, e.g., to suggest the user orient the sensor 34 away from the wall and into the center of the container, thereby enhancing the accuracy of the resulting temperature reading.

Optionally, the processor 20 may analyze the camera images to ensure that the user positions the sensor 34 at a desired distance from the container. For example, the processor 20 may provide visual confirmation on the display 28a when the sensor 34 is positioned within an acceptable range of distances from the container, e.g., since the sensor 34 may have optimal distances for acquiring accurate temperatures.

In another option, if the processor 20 does not automatically identify a food product from the images, the user may manually override and identify the food product. Such overrides may be communicated to the location electronic device 16 and/or server 14 (shown in FIG. 4) to help train the food identification engine within the database 15, e.g., for new food products. Similarly, if the processor 20 incorrectly misidentifies the food product, the user may manually override the error, which may be communicated to the server 14 to correct similar errors in the future.

In addition or alternatively, a probe 50 may be coupled to the apparatus 12 and inserted into a food product to acquire a temperature of the food product. For example, the infrared sensor 34a may be used to acquire temperatures of refrigerated food products, while the probe 50 may be used to acquire temperatures of heated food products (since the infrared sensor 34a may not accurately acquire temperatures of heated food products given that the surface temperature may not accurately reflect the overall temperature of heated food products). Optionally, the probe 50 may be cleaned such that the probe 50 may be inserted sequentially into different food products to acquire multiple temperature readings. Alternatively, a disposable sleeve (not shown) may be positioned over the probe 50, which may be removed after each temperature reading to allow the probe 50 to be used for multiple food products. In a further alternative, the probe 50 may be removed after each temperature reading and a new probe coupled to the apparatus 12 for each additional temperature reading. If the probe 50 is provided on a movable mount, such as the mount 48' shown in FIG. 3C, the probe 50 and mount 48' may be directed between the inactive and active positions, as desired, to acquire temperatures of appropriate products using either the infrared sensor 34' or the probe 50.'

Optionally, the processor 20 of the mobile device 10 (or within the temperature assembly 12 itself) may use object recognition and/or other algorithms to automatically recognize food products towards which the camera 24 is oriented. Upon identification of the food product recognized by the system, the system may direct the user, e.g., by presenting instructions on the display 28a, to use either the infrared sensor 34' to acquire a surface measurement of the food product, or to insert the temperature probe 50 into the food product to acquire temperature readings. For example, if the processor 20 identifies the food product as requiring the probe 50, the user may direct the mount 48' and probe 50 to the active position shown in FIG. 3C, and insert the probe 50 into an appropriate area of the food product. Optionally, additional instructions and/or guidelines may be presented on the display 28a, e.g., if the processor 20 recognizes that the probe 50 is not centered properly within a container of the food product. Similarly, if the processor 20 identifies the food product as requiring the infrared sensor 34', the mount 48' and probe 50 may be directed to the inactive position, and the infrared sensor 34' may be oriented towards an appropriate area of the food product, e.g., with instructions and/or guidelines presented on the display 20 to ensure temperature readings are properly acquired.

Once a series of temperatures is acquired, e.g., upon acquiring temperatures of all scheduled food products on the menu presented on the display 28a of the mobile electronic device 10, the processor 20 may transfer the data to a remote device, e.g., to the server 14 for storage in the database 15 and/or to the location electronic device 16. Alternatively, after each temperature/image is acquired, the processor 20 may transfer the data to the server 14 and/or location electronic device 16, thereby sending individual batches as each food product is selected from the menu.

Optionally, when one or more temperatures are acquired, the application may present one or more remedial actions or reminders to the user, e.g., on the display 28a of the mobile electronic device 10 and/or on a display of the location electronic device 16. For example, if the temperature of a refrigerated meat product is acquired, but is outside an accepted range, e.g., too warm, the user may be prompted immediately and suggested to act, e.g., turn down the thermostat on a refrigeration system associated with the container, check fluid or ice levels, and the like, as appropriate for the configuration of the location where the container is stored. Additional remedial actions may include putting the food item back into a refrigerator, discarding the food item, or any number of other instructions and steps. The process for remedial actions may include step by step procedures, e.g., through text, pictures, audio, or video information presented on the display 28a and/or location electronic device 16 as well as reminders and subsequent alerts and instructions in a pre-established sequence of events. Thus, this option may facilitate taking immediate action to troubleshoot potential problems before food products become spoiled or otherwise at risk.

Figure 8E:
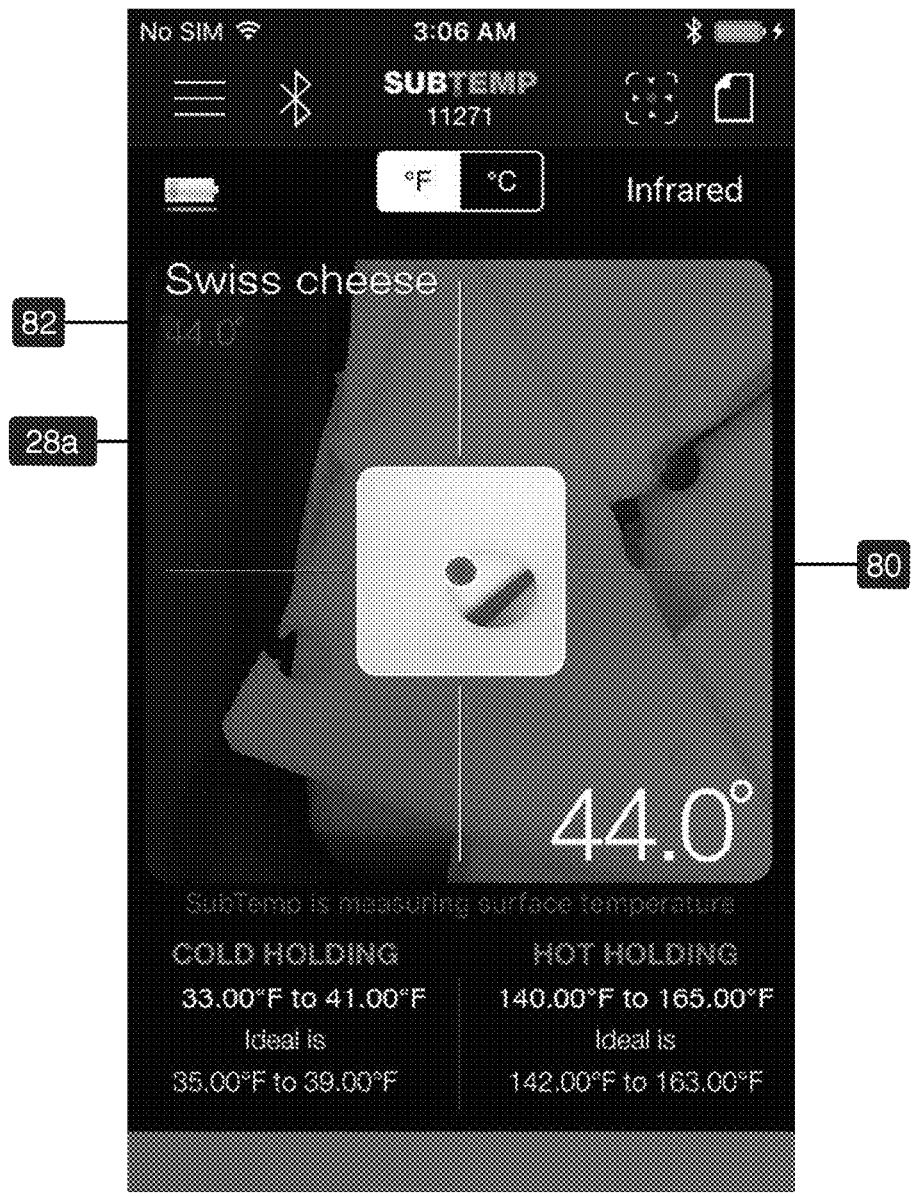

For example, FIGS. 8D-8E show a warning (e.g., by presenting result temperature 82 in red and/or other manner to draw attention to the user) indicating that the acquired temperature may be outside the desired range for the identified food product. Optionally, as shown, the desired range or ranges for the identified food product may be presented on the display 28a, e.g., adjacent real-time images and/or temperature readings, as shown.

In an exemplary method, if the remedial action required is placing a container of food product within a refrigerator, the processor 20 may activate a timer, e.g., for thirty minutes or other predetermined time period, to attempt to return the food product to within an acceptable temperature range. After the time elapses, the processor 20 may initiate acquiring a new temperature reading. If the temperature has been changed to within the acceptable range, the container may be returned to the preparation area; if not, the timer may be reset and the container placed again in the refrigerator; or ultimately, the processor may recommend disposal of the food product. Optionally, the processor 20 may prompt the user to take an image of the container in the refrigerator to ensure compliance with the remedial instructions.

Optionally, when remedial issues are raised by the processor, the electronic device 10 may provide messages, e.g., via wireless communications, to other electronic devices, e.g., to a manager and/or owner of the establishment, e.g. for informative purposes or for escalation purposes. These messages may include a record of the users involved with the remedial actions being undertaken as well as logs and/or images of the actions takes.

At any time, a report may be generated of the temperatures acquired using the system 8. For example, a user at the restaurant or other location where the temperatures were acquired may use the location electronic device 16 to generate a report of the temperatures, e.g., presenting the data on a display and/or printing a hard copy of the temperatures/images/time stamps, e.g., for a particular session, day, and/or other interval. Similarly, a manager, inspector, or other authorized person may access the data via the server 14 to generate desired reports from the location electronic device 16 or other remote device.

Thus, using the system 8, temperature records may be maintained to ensure that the acquired temperatures are properly taken for the associated food products. The image provides visual confirmation that the acquired temperature was taken for the actual food product identified from the menu. Thus, if a user acquired a temperature for an incorrect food product, a manager may identify the error easily since the image will not match the food product identified from the record. Such errors can then be remedied, e.g., by improving training of users or investigating intentional fraud.

In addition, the temperature sensing apparatus 12 may allow any compatible mobile electronic device to be used to acquire temperature data. For example, when not in use, the temperature sensing apparatus 12 may be stored at a desired location within the restaurant or other business, e.g., plugged in such that the power source 38 may be recharged. A user may unplug or otherwise prepare the apparatus 12, mount it to their mobile electronic device 10 (or alternatively to a dedicated mobile electronic device at the business), and then use the resulting system 8 to acquire temperature data, as described elsewhere herein.

Figure 9A:
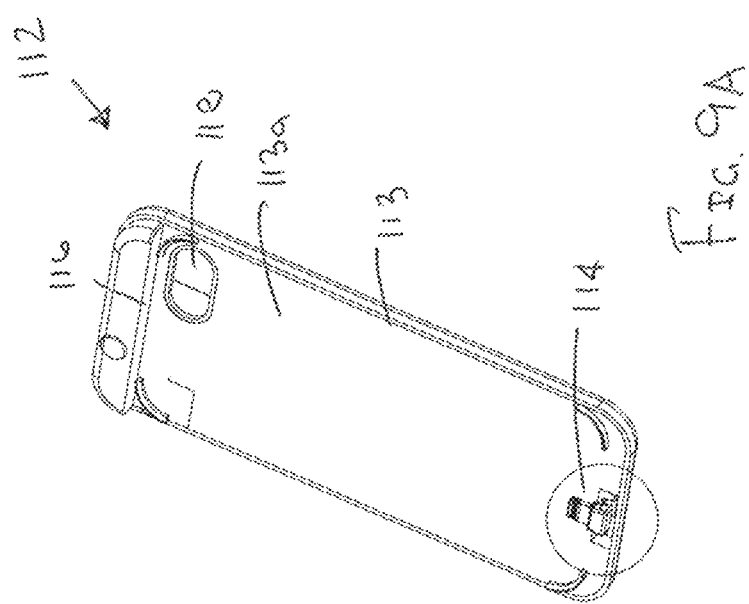

Turning now to FIGS. 9A-9C, another exemplary embodiment of a temperature assembly 112 is shown that may include features similar to other embodiments described elsewhere herein. Generally, the assembly 112 is carried by a case 113 that includes a recess or region 113a shaped and/or otherwise configured to at least partially receive a mobile electronic device 10, as best seen in FIG. 9B. The case 113 may include one or more mechanical and/or electrical connectors for removably coupling the electronic device to the case 113 to provide a system 108 that may be used similar to other embodiments herein. For example, as shown, the case 113 includes an electrical connector 114 that may be received in a corresponding connector on the electronic device 10, e.g., the charging and/or communication plug, to allow the assembly 112 to be controlled using the interface of the electronic device 10. The case 113 also includes a ledge 116 configured to capture the edge of the electronic device 10 opposite the connector 114, thereby providing an interference fit that secures the electronic device 10 in the recess 113a. Optionally, the case may include one or more sidewalls, tabs, and/or other features (not shown) that further engage the casing of the electronic device 10, as desired, to secure and/or protect the electronic device 10.

In addition, the case 113 includes an opening 118 located such that a camera 24 of the electronic device 10 is positioned in the opening 118 when the electronic device 10 is secured to the case 113, e.g., as shown in FIG. 9C. In this embodiment, instructions and/or data may be communicated between the electronic device 10 and the components of the assembly 112 via the connector 114. For example, the connector 114 may be coupled to an interface that communicates via the bus of the electronic device between the various components without using a wireless communications interface.

Similar to other embodiments, the assembly 112 includes a housing 142 carrying a temperature sensor including an infrared sensor 134a and a laser guide 134b mounted within or to the housing 142 to acquire temperature data along a line of sight of the sensor 134a. Optionally, the assembly 112 may also include a laser scanner 150, e.g., integrated into the housing 142 or coupled to the case 113 adjacent the housing 142. For example, the laser scanner 150 may include a laser device for transmitting laser light and a photodiode or other sensor (not shown) that may receive reflected laser light to identify barcodes positioned in front of the scanner 150.

In addition, the case includes a mount 148, e.g., formed into or attached to the housing 142, for receiving a temperature probe 50, similar to the housing 42' shown in FIG. 3C. The mount 148 is pivotable relative to the housing 142 and case 113 such that the probe 50 may be directed from an inactive or retracted position, e.g., where the probe 50 extends along the case 113, as shown in FIG. 9C, and one or more active positions. For example, FIG. 9D shows an active position where the probe 50 extends substantially perpendicularly from the case 113, e.g., about ninety degrees (90°), such that a tip 52 of the probe 50 is within the field of view of the camera 24.

Optionally, as shown in FIG. 9E, the mount 148 may be directed to a second active position where the probe 50 is oriented away from the case 113, e.g., about one hundred eighty degrees (180°) from the inactive position. The second active position may be useful for acquiring temperature data for contents of particularly hot containers since the user may be able to insert the tip into the container without holding the system 8 directly above the container, which may be uncomfortably hot.

When the mount 148 is in the inactive position, the infrared sensor 134a may be active and used to acquire temperature data, as described elsewhere herein. When the mount 148 is directed towards one of the active positions, the infrared sensor 134a may be automatically deactivated and the probe 50 may be activated. Optionally, the probe 50 may only be activated when the mount 148 is positioned in the first or second active positions, i.e., to ensure that the probe 50 is oriented properly. Optionally, the mount 148 may include one or more detents or features that resist movement of the mount 148 when it reaches the first or second active positions, e.g., to secure the probe 50 relative to the housing 142 and/or provide tactile feedback to the user. Thus, the user 148 may feel the mount 148 reaching the active position when the features engage, but may overcome the resistance to move the mount 148 and probe 50 to another position, e.g., back to the inactive position.

Images of the tip 52 of the probe 50 and/or the field of view of the infrared sensor 134 may be presented in images from the camera 24 on a display 28*a* of the electronic device 10, similar to other embodiments herein. Thus, the location of where to insert the probe 50 and/or where to point the infrared sensor 134*a* may be presented on the display 28*a* in real-time to the user to ensure proper orientation when temperatures readings are acquired. Otherwise, the system 108 may operate and/or include various features and/or functionality similar to other embodiments described elsewhere herein.

Turning to FIGS. 10A-10D, another example of a system 208 is shown for acquiring temperature data that includes a temperature sensing assembly 212 integrated into the casing 213 of a mobile electronic device 210. The electronic device 210 generally includes components similar to the electronic device 10 described elsewhere herein, e.g., one or more processors, memory, communications interfaces, and the like (not shown). In addition, the electronic device 210 includes a display 228*a*, e.g., providing a user interface, and camera 224 opposite the display 228*a* on the casing 213, also similar to other embodiments herein.

Unlike previous embodiments, the temperature sensing assembly 212 is integrated into or otherwise permanently attached to the casing 213. Similar to other embodiments, however, the assembly 212 includes a housing 242 carrying an infrared sensor 234*a* and laser guide 234*b*, and a mount 248 to which a temperature probe 50 may be coupled. Similar to other embodiments, the mount 248 may be pivotable from inactive position where the probe 50 is located adjacent the casing 213, shown in FIG. 10A, to one or more active positions, e.g., a first active position shown in FIG. 10B where the probably is oriented substantially perpendicular to the casing 213 to position the tip 52 in the field of view of the camera 224, and, optionally, a second active position shown in FIGS. 10C and 10D, where the probe 50 is oriented away from the case 213, e.g., about one hundred eighty degrees (180°) from the inactive position.

Given that the temperature assembly 212 is integrated into the device 210, the assembly 212 may not need its own processor, power source, and/or communications interface. Instead, the processor of the device 210 may control operation of the components and/or receive temperature data directly from the infrared sensor 234*a* and/or probe 50 via its normal protocols.

Optionally, similar to other embodiments herein, the assembly 212 may also include a laser scanner 250, e.g., integrated into the housing 242 or coupled to the casing 213 adjacent the housing 242. Thus, in addition to acquiring temperature data, a user may select an option using the interface 228*a* of the device 210 and the processor may control operation of the scanner 250 to read barcodes. The processor may acquire data from memory and/or may communicate with external devices, e.g., a location electronic device 16 and/or server 14 (not shown, see FIG. 4) based on the barcode and provide information on the display to the user 228*a*.

Turning to FIGS. 11A-11H, another example of a system 308 is shown for acquiring temperature data that includes a modular temperature sensing assembly 312 that may be selectively mounted to a mobile electronic device 310. As best seen in FIGS. 11A and 11B, the electronic device 310 generally includes components similar to other electronic devices described elsewhere herein, e.g., one or more processors, memory, communications interfaces, and the like (not shown).

In addition, the electronic device 310 includes a display 328*a*, e.g., providing a user interface, and camera 324 opposite the display 328*a*, also similar to other embodiments herein. Optionally, the device 310 may also include a laser scanner 350, e.g., located adjacent the camera 324. Unlike the previous embodiments, the electronic device 310 also includes an electrical connector 314, e.g., on the casing 313 opposite the display 328*a*.

The temperature assembly 312 includes separate subassemblies that may be selectively coupled to the electronic device 310, e.g., via the connector 314, e.g., a temperature probe assembly 348, and an infrared temperature sensing assembly 342. For example, as shown in FIGS. 11C-11E, the temperature probe assembly 348 includes a housing 348*a* configured to be mounted to the casing 313 and a mount 348*b* pivotally coupled to the housing 348*a* for receiving a temperature probe 50, similar to other embodiments herein. In the embodiment shown, the housing 348*a* includes a bottom surface that includes a first mating connector (not shown) configured to be coupled to the connector 314 on the casing 313, and a top surface opposite the bottom surface including a second connector 348*c*, which may be similar in configuration to the connector 314. The connectors 314 may have sufficient mechanical interaction to secure the housing 348*a* to the casing 313. Optionally, the housing 348*a* may include one or more additional connectors, e.g., a bracket and/or other mechanical connector for removably securing the housing 348 to the casing 313, e.g., similar to the brackets shown in FIGS. 7A-7G.

As shown in FIGS. 11F-11H, the infrared temperature sensing assembly 342 generally includes housing 342*a* carrying an infrared sensor 334*a* and laser guide 334*b*, similar to other embodiments herein. The housing 342*a* includes bottom surface including a mating connector (not shown) configured to be coupled to the connector 314 or the second connector 348*c*.

Thus, as shown in FIGS. 11C-11E, the temperature probe assembly 348 may be mounted to the electronic device 310, e.g., via connector 314 and the first mating connector (not shown) and used to acquire temperature data using the probe 50 without requiring the infrared temperature sensing assembly 342. If the infrared temperature sensing assembly 342 is also needed, as shown in FIGS. 11F-11H, the infrared temperature sensing assembly 342 may be coupled to the housing 348*a*, e.g., via the second connector 348*a* and the second mating connector (not shown). In this manner, the probe 50 may be selectively directed between the inactive position shown in FIGS. 11C-11E and the active position shown in FIG. 11H depending on whether the infrared sensor 334*a* or the probe 50 are being used to acquire the temperature data, similar to other embodiments herein.

In addition, this configuration allows the infrared temperature sensing assembly 342 to be mounted directly to the electronic device 310 (i.e., without the temperature probe assembly 348) and used to acquire temperature data using the infrared sensor 334*a*. Optionally, one or more mechanical connectors (not shown) may be provided on the different components if desired, e.g., to further secure the desired components together temporarily during use.

Similar to the previous embodiments, the subassemblies 342, 348 may not need their own processor, power source, and/or communications interface since the processor of the electronic device 310 may control operation of the components and/or receive temperature data directly from the infrared sensor 334a and/or probe 50. Further, without either of the subassemblies 342, 348, the electronic device 310 may be used as a barcode scanner using the scanner 350, if desired, similar to other embodiments herein.

Although the exemplary embodiments described above relate to systems and methods for acquiring temperature data for food products, it will be appreciated that a modular temperature sensing apparatus and associated software application may be used with mobile electronic devices to acquire temperatures for other objects as well, e.g., surfaces of food preparation areas, surfaces or equipment within manufacturing facilities, and the like, where it may be desirable to acquire real-time temperature readings. Thus, the systems and methods herein may allow users to acquire real-time temperatures and images of objects simply using a conventional smart mobile device. The resulting data may be stored locally, transmitted to a remote server or other location, and/or analyzed, as desired.

While the invention is susceptible to various modifications, and alternative forms, specific examples thereof have been shown in the drawings and are herein described in detail. It should be understood that the invention is not to be limited to the particular forms or methods disclosed, but to the contrary, the invention is to cover all modifications, equivalents and alternatives falling within the scope of the appended claims.

I claim:

1. A method for logging temperatures of food products at a physical location, comprising:
   providing a mobile electronic device including a camera and carrying a temperature assembly including a mount carrying an elongate temperature probe;
   directing the mount from an inactive position to an active position where a tip of the probe lies within a field of the view of the camera;
   inserting the tip of the temperature probe into a food product in a container; and
   activating the mobile electronic device to acquire a temperature of the food product using the temperature probe and substantially simultaneously acquiring an image of the food product using the camera.

2. The method of claim 1, wherein the tip of the probe is outside the field of view of the camera in the inactive position.

3. The method of claim 1, wherein the temperature assembly further comprises an infrared sensor, the method further comprising:
   directing the mount to the inactive position, thereby deactivating the temperature probe and activating the infrared sensor;
   orienting the infrared sensor towards a container including a second food product; and
   acquiring a temperature of the second food product with the infrared sensor and an image of the food product with the camera.

4. A method for acquiring temperature data of food products, comprising:
   providing a mobile electronic device and a temperature assembly including a temperature probe coupled to the mobile electronic device;
   directing the temperature probe towards a container including a food product, whereupon the food product is automatically identified on a display of the mobile electronic device; and
   activating the mobile electronic device to acquire a temperature of the identified food product using the temperature probe and substantially simultaneously acquire an image using a camera of the mobile electronic device of the food product.

5. The method of claim 4, wherein object recognition is used to automatically identify the food product based on the image acquired using the camera and wherein the user is prompted to confirm that the correct food product has been identified before activating the mobile electronic device to acquire the temperature.

6. A method for acquiring temperature data of a remote object, comprising:
   providing a temperature assembly carried by a mobile electronic device such that an infrared sensor of the temperature assembly is aligned with a field of view of a camera of the mobile electronic device;
   orienting the infrared sensor towards a target object; and
   acquiring one or more temperature samples to obtain a temperature of the object with the infrared sensor and an image of the object with the camera.

7. The method of claim 6, wherein multiple temperature samples are acquired and wherein the temperature is an average of the temperature samples.

8. A method for acquiring temperature data of food products, comprising:
   providing a temperature assembly carried by a mobile electronic device such that an infrared sensor of the temperature assembly is aligned with a field of view of a camera of the mobile electronic device;
   orienting the infrared sensor towards a container including a food product;
   automatically identifying the food product based on images presented on the display;
   acquiring a temperature of the food product with the infrared sensor and an image of the food product with the camera.

9. The method of claim 8, further comprising presenting an identifier presented on the display along with an image of the food product acquired from the camera indicating a direction in which the infrared sensor is oriented such that the user may confirm that the infrared sensor is oriented towards the desired food product.

* * * * *